US009556090B2

(12) United States Patent
Wang et al.

(10) Patent No.: US 9,556,090 B2
(45) Date of Patent: Jan. 31, 2017

(54) METHOD FOR THE PREPARATION OF TRICHLOROMETHYL-GROUP-SUBSTITUTED BENZENE

(71) Applicant: Shanghai Fanglun New Material Technology Co., Ltd., Shanghai (CN)

(72) Inventors: Nongyue Wang, Shanghai (CN); Xiongwei Qu, Tianjin (CN); Guohua Li, Tianjin (CN); Quanzhong Zhao, Shanghai (CN); Jianming Shao, Shanghai (CN); Guoqiang Wen, Shanghai (CN)

(73) Assignee: Shanghai Fanglun New Material Technology Co., Ltd., Shanghai (CN)

( * ) Notice: Subject to any disclaimer, the term of this patent is extended or adjusted under 35 U.S.C. 154(b) by 0 days.

(21) Appl. No.: 14/905,775

(22) PCT Filed: Sep. 12, 2014

(86) PCT No.: PCT/CN2014/086372
§ 371 (c)(1),
(2) Date: Jan. 15, 2016

(87) PCT Pub. No.: WO2015/035937
PCT Pub. Date: Mar. 19, 2015

(65) Prior Publication Data
US 2016/0152533 A1 Jun. 2, 2016

(30) Foreign Application Priority Data

Sep. 13, 2013 (CN) .......................... 2013 1 0422286
Jul. 8, 2014 (CN) ...................... 2014 2 0373955 U

(51) Int. Cl.
*C07C 17/14* (2006.01)
*C07C 51/60* (2006.01)
(Continued)

(52) U.S. Cl.
CPC ............. *C07C 17/08* (2013.01); *C07C 17/093* (2013.01); *C07C 17/12* (2013.01); *C07C 17/14* (2013.01); *C07C 17/383* (2013.01); *C07C 51/60* (2013.01)

(58) Field of Classification Search
CPC ......... C07C 17/093; C07C 17/14; C07C 51/60
See application file for complete search history.

(56) References Cited

U.S. PATENT DOCUMENTS 1,345,373 A 7/1920 Kyrides
1,384,909 A 7/1921 Loomis
(Continued)

FOREIGN PATENT DOCUMENTS

CN 1948245 A 4/2007
CN 200942338 Y 9/2007
(Continued)

OTHER PUBLICATIONS

JP 2010013388 A, Jan. 2010, pp. 1-15; English translation.*
(Continued)

*Primary Examiner* — Jafar Parsa
*Assistant Examiner* — Medhanit Bahta
(74) *Attorney, Agent, or Firm* — Mei & Mark LLP; Manni Li

(57) ABSTRACT

The present application relates to a method for photochlorination, and specifically to photochlorination by a photochemical reaction of an aromatic compound with gaseous chlorine so as to prepare a trichloromethyl-substituted benzene, and to a method using bis-(trichloromethyl)-benzene as the trichloromethyl-substituted benzene to prepare by further reaction bis-(chloroformyl)-benzene. Through the control of temperature, illuminance and consumption of gaseous chlorine, the method of this application can greatly improve the purity of trichloromethyl-substituted benzene (Continued)

and further prepare polymer-grade bis-(chloroformyl)-benzene with low cost. The present application also relates to a method for purifying trichloromethyl-substituted benzene, and specifically to a method for purifying trichloromethyl-substituted benzene via molecular distillation. The present application further relates to a photochlorination reactor for use in photochlorination reactions (such as those of the present application).

25 Claims, 17 Drawing Sheets

(51) Int. Cl.
    *C07C 17/093*     (2006.01)
    *C07C 17/08*     (2006.01)
    *C07C 17/12*     (2006.01)
    *C07C 17/383*     (2006.01)

(56) References Cited

U.S. PATENT DOCUMENTS

| | | | |
|---|---|---|---|
| 1,733,268 A | 10/1929 | Kydrides | |
| 2,034,962 A | 3/1936 | Smith | |
| 2,654,789 A | 10/1953 | Ligett | |
| 2,695,873 A | 11/1954 | Loverde | |
| 2,817,632 A | 12/1957 | Mayor | |
| 2,844,635 A | 7/1958 | Mayor | |
| 3,363,013 A | 1/1968 | Kyker | |
| 4,029,560 A | 6/1977 | Yoshinaka et al. | |
| 4,046,656 A * | 9/1977 | Davis | C07B 39/00 204/157.79 |
| 4,048,033 A | 9/1977 | Yoshinaka et al. | |
| 5,514,254 A | 5/1996 | Ribaldo | |
| 2001/0014759 A1 | 8/2001 | Marhold et al. | |
| 2016/0008786 A1 | 1/2016 | Jasra et al. | |

FOREIGN PATENT DOCUMENTS

| | | | |
|---|---|---|---|
| CN | 101066926 A | | 11/2007 |
| CN | 102211975 A | | 10/2011 |
| CN | 102344362 A | | 2/2012 |
| CN | 101456788 B | | 5/2012 |
| CN | 102516060 A | | 6/2012 |
| DE | 3146868 A1 | | 7/1982 |
| GB | 1442122 A | | 7/1976 |
| GB | 1483690 A | | 8/1977 |
| JP | 34010015 | * | 11/1959 |
| JP | 57-130931 A | | 8/1982 |
| JP | S61-218536 A | | 9/1986 |
| JP | 2010013388 A | * | 1/2010 |

OTHER PUBLICATIONS

CN1948245A, Apr. 2006, pp. 1-5; English translation.*
JP34010015, Nov. 1959, p. 1; English Abstract.*
Zhang, J. et al. The Synthesis of p-Fluorobenzoyl Chloride, Organo-Fluorine Industry, Apr. 2011, pp. 46-47; with English translation.*
Wang Lumin et al., "SS," Journal of Tonghua Normal Univeristy, 2005, 26(4): 46-47.

* cited by examiner

Area Percent Report

Data file: D : \m-hexachloro\98-3.dat  
Method: E : \7820\method\hexachloro.met  
Acquisition Time: 2012-8-26 20:28:13 (GMT +08:00)

| Rear Signal Result Retention time | Area | Area Percent | Peak Height | Peak Height Percent |
|---|---|---|---|---|
| 2.753 | 3100 | 0.00 | 1630 | 0.00 |
| 3.133 | 2122 | 0.00 | 1303 | 0.00 |
| 4.173 | 3404 | 0.00 | 1697 | 0.01 |
| 4.887 | 2337 | 0.00 | 1292 | 0.00 |
| 5.547 | 1483 | 0.00 | 985 | 0.00 |
| 5.877 | 2910 | 0.00 | 1527 | 0.00 |
| 6.583 | 55752 | 0.04 | 31714 | 0.09 |
| 6.947 | 15889 | 0.01 | 9383 | 0.03 |
| 7.083 | 12374 | 0.01 | 7173 | 0.02 |
| 7.220 | 4412 | 0.00 | 2336 | 0.01 |
| 7.410 | 2100 | 0.00 | 945 | 0.00 |
| 7.667 | 4311 | 0.00 | 2277 | 0.01 |
| 7.803 | 5963 | 0.00 | 1935 | 0.01 |
| 8.040 | 43094 | 0.03 | 23222 | 0.07 |
| 8.280 | 617871 | 0.43 | 345001 | 1.03 |
| 8.423 | 7387 | 0.01 | 2037 | 0.01 |
| 8.643 | 81789 | 0.06 | 42329 | 0.13 |
| 8.737 | 486139 | 0.34 | 245731 | 0.73 |
| 8.950 | 22394 | 0.02 | 9208 | 0.03 |
| 9.173 | 18729 | 0.01 | 4207 | 0.01 |
| 9.293 | 6835 | 0.00 | 3038 | 0.01 |
| 9.490 | 140381317 | 97.61 | 31638379 | 94.41 |
| 9.673 | 276614 | 0.19 | 157192 | 0.47 |
| 9.770 | 114981 | 0.08 | 64692 | 0.19 |
| 9.883 | 19765 | 0.01 | 7126 | 0.02 |
| 10.040 | 2317 | 0.00 | 1060 | 0.00 |
| 10.100 | 160903 | 0.11 | 87515 | 0.26 |
| 10.317 | 113708 | 0.08 | 64438 | 0.19 |

| | | | | |
|---|---|---|---|---|
| 10.393 | 10907 | 0.01 | 4494 | 0.01 |
| 10.613 | 37542 | 0.03 | 20759 | 0.06 |
| 10.700 | 1029876 | 0.72 | 588302 | 1.76 |
| 10.763 | 12852 | 0.01 | 7459 | 0.02 |
| 10.863 | 32143 | 0.02 | 17369 | 0.05 |
| 10.967 | 5372 | 0.00 | 2641 | 0.01 |
| 11.080 | 6004 | 0.00 | 2935 | 0.01 |
| 11.177 | 2285 | 0.00 | 1259 | 0.00 |
| 11.317 | 10936 | 0.01 | 4963 | 0.01 |
| 11.393 | 5004 | 0.00 | 2187 | 0.01 |
| 11.450 | 84129 | 0.06 | 41432 | 0.12 |
| 11.583 | 45385 | 0.03 | 24012 | 0.07 |
| 11.723 | 1133 | 0.00 | 408 | 0.00 |
| 11.817 | 39572 | 0.03 | 21405 | 0.06 |
| 11.943 | 1754 | 0.00 | 770 | 0.00 |
| 12.087 | 5372 | 0.00 | 1954 | 0.01 |
| 12.247 | 9231 | 0.01 | 3889 | 0.01 |
| 12.313 | 4284 | 0.00 | 1843 | 0.01 |
| 12.570 | 2827 | 0.00 | 1229 | 0.00 |
| 12.687 | 1227 | 0.00 | 413 | 0.00 |
| 13.030 | 1535 | 0.00 | 753 | 0.00 |
| 13.200 | 4991 | 0.00 | 1504 | 0.00 |
| Total | 143824361 | 100.00 | 33511352 | 100.00 |

FIG. 1 Continued

Area Percent Report

Data file: D : \m-acetylchloride\122-1.dat
Method: E : \7820\method\acetylchloride.met
Acquisition Time: 2013-5-6 19:29:37 (GMT +08:00)

| Rear Signal Result Retention time | Area | Area Percent | Peak Height | Peak Height Percent |
|---|---|---|---|---|
| 3.587 | 1441 | 0.00 | 638 | 0.01 |
| 4.120 | 3241 | 0.01 | 1351 | 0.01 |
| 4.587 | 49517550 | 99.97 | 11836570 | 99.95 |
| 5.533 | 2741 | 0.01 | 1274 | 0.01 |
| 5.863 | 3264 | 0.01 | 951 | 0.01 |
| 6.680 | 3070 | 0.01 | 1377 | 0.01 |
| 7.503 | 1051 | 0.00 | 509 | 0.00 |
| Total | 49532358 | 100.00 | 11842670 | 100.00 |

Area Percent Report

Data file: D:\p-hexachloro\70-3.dat
Method: E:\7820\method\hexachloro.met
Acquisition Time: 2013-4-25 11:08:41 (GMT +08:00)

| Rear Signal Result Retention time | Area | Area Percent | Peak Height | Peak Height Percent |
|---|---|---|---|---|
| 2.190 | 54863 | 0.02 | 49225 | 0.12 |
| 2.773 | 3184 | 0.00 | 1896 | 0.00 |
| 3.713 | 5465 | 0.00 | 2446 | 0.01 |
| 4.067 | 215211 | 0.10 | 125971 | 0.31 |
| 4.187 | 4206 | 0.00 | 1525 | 0.00 |
| 5.100 | 5727 | 0.00 | 2517 | 0.01 |
| 5.150 | 1859 | 0.00 | 731 | 0.00 |
| 5.323 | 15772 | 0.01 | 8708 | 0.02 |
| 5.897 | 2098 | 0.00 | 1010 | 0.00 |
| 6.053 | 2709 | 0.00 | 826 | 0.00 |
| 6.580 | 157969 | 0.07 | 91684 | 0.23 |
| 6.653 | 115118 | 0.05 | 65399 | 0.16 |
| 6.847 | 25136 | 0.01 | 12703 | 0.03 |
| 6.990 | 8337 | 0.00 | 3704 | 0.01 |
| 7.113 | 4427 | 0.00 | 2222 | 0.01 |
| 7.287 | 1120 | 0.00 | 363 | 0.00 |
| 7.420 | 1828 | 0.00 | 733 | 0.00 |
| 7.693 | 22593 | 0.01 | 11974 | 0.03 |
| 7.820 | 3877 | 0.00 | 1676 | 0.00 |
| 7.960 | 2950 | 0.00 | 1258 | 0.00 |
| 8.067 | 16678 | 0.01 | 9170 | 0.02 |
| 8.307 | 1932 | 0.00 | 727 | 0.00 |
| 8.433 | 573231 | 0.25 | 323613 | 0.80 |
| 8.667 | 15739 | 0.01 | 7015 | 0.02 |
| 8.757 | 240014 | 0.11 | 82690 | 0.20 |
| 9.067 | 4007 | 0.00 | 947 | 0.00 |
| 9.183 | 10969 | 0.00 | 5068 | 0.01 |
| 9.267 | 99072 | 0.04 | 41465 | 0.10 |

| | | | | |
|---:|---:|---:|---:|---:|
| 9.330 | 10555 | 0.00 | 5021 | 0.01 |
| 9.393 | 140353 | 0.06 | 59400 | 0.15 |
| 9.933 | 220472017 | 97.75 | 38700784 | 95.09 |
| 10.063 | 20196 | 0.01 | 9133 | 0.02 |
| 10.427 | 1482 | 0.00 | 501 | 0.00 |
| 10.500 | 2423 | 0.00 | 1565 | 0.00 |
| 10.720 | 3985 | 0.00 | 2287 | 0.01 |
| 10.787 | 83517 | 0.04 | 47390 | 0.12 |
| 10.873 | 14342 | 0.01 | 7415 | 0.02 |
| 10.923 | 25593 | 0.01 | 13161 | 0.03 |
| 11.027 | 985781 | 0.44 | 544030 | 1.34 |
| 11.103 | 51503 | 0.02 | 24884 | 0.06 |
| 11.190 | 1128 | 0.00 | 479 | 0.00 |
| 11.393 | 57998 | 0.03 | 31420 | 0.08 |
| 11.477 | 30861 | 0.01 | 14024 | 0.03 |
| 11.523 | 11826 | 0.01 | 4972 | 0.01 |
| 11.597 | 4814 | 0.00 | 1951 | 0.00 |
| 11.667 | 4123 | 0.00 | 1404 | 0.00 |
| 11.803 | 22963 | 0.01 | 9082 | 0.02 |
| 11.893 | 1445 | 0.00 | 693 | 0.00 |
| 11.967 | 9242 | 0.00 | 3557 | 0.01 |
| 12.030 | 73143 | 0.03 | 38032 | 0.09 |
| 12.130 | 26570 | 0.01 | 13043 | 0.03 |
| 12.363 | 199844 | 0.09 | 96678 | 0.24 |
| 12.457 | 11940 | 0.01 | 3063 | 0.01 |
| 12.627 | 212198 | 0.09 | 72957 | 0.18 |
| 12.727 | 13260 | 0.01 | 3941 | 0.01 |
| 12.810 | 24157 | 0.01 | 4209 | 0.01 |
| 12.943 | 33987 | 0.02 | 10125 | 0.02 |
| 13.033 | 12986 | 0.01 | 3204 | 0.01 |
| 13.143 | 20757 | 0.01 | 4558 | 0.01 |
| 13.200 | 8444 | 0.00 | 2900 | 0.01 |
| 13.303 | 16299 | 0.01 | 3153 | 0.01 |
| 13.653 | 1314666 | 0.58 | 104513 | 0.26 |
| 19.263 | 2007 | 0.00 | 374 | 0.00 |
| Total | 225542496 | 100.00 | 40701169 | 100.00 |

FIG. 3 Continued

Area Percent Report

Data file: D:\p-acetylchloride\89-1.dat
Method: E:\7820\method\acetylchloride.met
Acquisition Time: 2013-5-31 20:53:28 (GMT +08:00)

| Rear Signal Result Retention time | Area | Area Percent | Peak Height | Peak Height Percent |
|---|---|---|---|---|
| 4.350 | 4774843 | 99.96 | 2300874 | 99.97 |
| 4.477 | 660 | 0.01 | 275 | 0.01 |
| 4.553 | 248 | 0.00 | 126 | 0.00 |
| 5.650 | 2347 | 0.03 | 693 | 0.02 |
| 6.590 | 200 | 0.00 | 137 | 0.00 |
| Total | 4822698 | 100.00 | 2321605 | 100.00 |

Area Percent Report

Data file: D:\m-hexachloro\110.dat
Method: E:\7820\method\hexachloro.met
Acquisition Time: 2012-9-24 20:37:28 (GMT +08:00)

| Rear Signal Result Retention time | Area | Area Percent | Peak Height | Peak Height Percent |
|---|---|---|---|---|
| 2.060 | 4798 | 0.00 | 3792 | 0.00 |
| 2.163 | 1336 | 0.00 | 1066 | 0.00 |
| 2.420 | 1020 | 0.00 | 467 | 0.00 |
| 2.753 | 83563 | 0.02 | 52305 | 0.04 |
| 3.133 | 93259 | 0.02 | 56845 | 0.04 |
| 3.213 | 1152 | 0.00 | 542 | 0.00 |
| 3.487 | 1078 | 0.00 | 698 | 0.00 |
| 3.550 | 4813 | 0.00 | 2913 | 0.00 |
| 3.640 | 3847 | 0.00 | 1291 | 0.00 |
| 3.993 | 5256 | 0.00 | 3382 | 0.00 |
| 4.170 | 46222 | 0.01 | 24487 | 0.02 |
| 4.283 | 1568 | 0.00 | 586 | 0.00 |
| 4.667 | 3664 | 0.00 | 2155 | 0.00 |
| 4.887 | 35937 | 0.01 | 18877 | 0.01 |
| 5.073 | 5961 | 0.00 | 2493 | 0.00 |
| 5.153 | 102579 | 0.02 | 49938 | 0.04 |
| 5.250 | 7580 | 0.00 | 2382 | 0.00 |
| 5.360 | 1751 | 0.00 | 744 | 0.00 |
| 5.423 | 2135 | 0.00 | 790 | 0.00 |
| 5.553 | 1042 | 0.00 | 399 | 0.00 |
| 5.603 | 3239 | 0.00 | 1839 | 0.00 |
| 5.703 | 2003 | 0.00 | 1113 | 0.00 |
| 5.780 | 2135 | 0.00 | 1098 | 0.00 |
| 5.877 | 22047 | 0.01 | 10426 | 0.01 |
| 5.947 | 59620 | 0.01 | 34562 | 0.03 |
| 6.040 | 14761 | 0.00 | 8342 | 0.01 |
| 6.137 | 179764 | 0.04 | 101018 | 0.08 |
| 6.247 | 5003 | 0.00 | 1417 | 0.00 |

| | | | | |
|---|---|---|---|---|
| 6.477 | 54375 | 0.01 | 22959 | 0.02 |
| 6.560 | 41229 | 0.01 | 14731 | 0.01 |
| 6.673 | 10696 | 0.00 | 5282 | 0.00 |
| 6.723 | 18468 | 0.00 | 9452 | 0.01 |
| 6.847 | 13380 | 0.00 | 6622 | 0.01 |
| 6.960 | 2736658 | 0.65 | 1547849 | 1.22 |
| 7.067 | 49775 | 0.01 | 16586 | 0.01 |
| 7.150 | 7424 | 0.00 | 2982 | 0.00 |
| 7.213 | 43529 | 0.01 | 17578 | 0.01 |
| 7.303 | 35396 | 0.01 | 18186 | 0.01 |
| 7.353 | 26985 | 0.01 | 10139 | 0.01 |
| 7.413 | 11799 | 0.00 | 5587 | 0.00 |
| 7.470 | 23155 | 0.01 | 8945 | 0.01 |
| 7.537 | 454552 | 0.11 | 148377 | 0.12 |
| 7.643 | 33625 | 0.01 | 11050 | 0.01 |
| 7.837 | 10688699 | 2.53 | 5390532 | 4.24 |
| 7.980 | 1019874 | 0.24 | 369233 | 0.29 |
| 8.120 | 100704 | 0.02 | 41165 | 0.03 |
| 8.190 | 181109 | 0.04 | 78087 | 0.06 |
| 8.310 | 13576640 | 3.22 | 6229727 | 4.90 |
| 8.470 | 25047036 | 5.94 | 10963690 | 8.63 |
| 8.627 | 2802850 | 0.66 | 855565 | 0.67 |
| 8.753 | 488340 | 0.12 | 207660 | 0.16 |
| 8.833 | 539126 | 0.13 | 100118 | 0.08 |
| 9.050 | 113509563 | 26.91 | 29140124 | 22.94 |
| 9.250 | 11026987 | 2.61 | 3164113 | 2.49 |
| 9.507 | 165758676 | 39.30 | 35401567 | 27.87 |
| 9.557 | 694982 | 0.16 | 482661 | 0.38 |
| 9.620 | 25943 | 0.01 | 10766 | 0.01 |
| 9.727 | 26949928 | 6.39 | 11344936 | 8.93 |
| 9.793 | 246960 | 0.06 | 148956 | 0.12 |
| 9.863 | 511950 | 0.12 | 237587 | 0.19 |
| 9.947 | 8319602 | 1.97 | 4502163 | 3.54 |
| 10.057 | 398392 | 0.09 | 187635 | 0.15 |
| 10.170 | 597068 | 0.14 | 250851 | 0.20 |
| 10.220 | 104895 | 0.02 | 59778 | 0.05 |
| 10.337 | 3655031 | 0.87 | 2060355 | 1.62 |
| 10.420 | 3790991 | 0.90 | 1766589 | 1.39 |
| 10.477 | 267639 | 0.06 | 142179 | 0.11 |
| 10.627 | 559311 | 0.13 | 166635 | 0.13 |
| 10.717 | 4723187 | 1.12 | 2495012 | 1.96 |
| 10.770 | 544024 | 0.13 | 305746 | 0.24 |
| 10.880 | 3883034 | 0.92 | 1706289 | 1.34 |
| 10.980 | 1339506 | 0.32 | 708645 | 0.56 |
| 11.037 | 249549 | 0.06 | 119721 | 0.09 |
| 11.087 | 647555 | 0.15 | 317169 | 0.25 |
| 11.187 | 563044 | 0.13 | 284932 | 0.22 |
| 11.270 | 95233 | 0.02 | 46820 | 0.04 |
| 11.327 | 809770 | 0.19 | 430929 | 0.34 |
| 11.370 | 155564 | 0.04 | 89084 | 0.07 |
| 11.460 | 504253 | 0.12 | 157961 | 0.12 |
| 11.530 | 1786588 | 0.42 | 723105 | 0.57 |
| 11.643 | 320768 | 0.08 | 149024 | 0.12 |

FIG. 5 Continued

| | | | | |
|---|---|---|---|---|
| 11.697 | 738612 | 0.18 | 172308 | 0.14 |
| 11.780 | 223791 | 0.05 | 115429 | 0.09 |
| 11.823 | 709440 | 0.17 | 217084 | 0.17 |
| 11.973 | 1309417 | 0.31 | 471363 | 0.37 |
| 12.107 | 1171749 | 0.28 | 506318 | 0.40 |
| 12.200 | 695096 | 0.16 | 247898 | 0.20 |
| 12.267 | 1646530 | 0.39 | 863357 | 0.68 |
| 12.357 | 87167 | 0.02 | 35159 | 0.03 |
| 12.453 | 865464 | 0.21 | 214617 | 0.17 |
| 12.577 | 349222 | 0.08 | 99505 | 0.08 |
| 12.700 | 107274 | 0.03 | 29211 | 0.02 |
| 12.773 | 235576 | 0.06 | 99996 | 0.08 |
| 12.843 | 143056 | 0.03 | 52132 | 0.04 |
| 12.993 | 1123144 | 0.27 | 357005 | 0.28 |
| 13.043 | 269927 | 0.06 | 117466 | 0.09 |
| 13.153 | 364789 | 0.09 | 93118 | 0.07 |
| 13.287 | 65165 | 0.02 | 24924 | 0.02 |
| 13.347 | 37010 | 0.01 | 15042 | 0.01 |
| 13.450 | 175818 | 0.04 | 62905 | 0.05 |
| 13.677 | 242850 | 0.06 | 78197 | 0.06 |
| 13.763 | 45180 | 0.01 | 17553 | 0.01 |
| 13.877 | 64893 | 0.02 | 24690 | 0.02 |
| 13.973 | 5444 | 0.00 | 2503 | 0.00 |
| 19.150 | 1418 | 0.00 | 364 | 0.00 |
| 19.343 | 7119 | 0.00 | 1164 | 0.00 |
| 19.750 | 28377 | 0.01 | 4108 | 0.00 |
| 20.010 | 77542 | 0.02 | 4863 | 0.00 |
| 20.487 | 51432 | 0.01 | 5069 | 0.00 |
| 21.157 | 69936 | 0.02 | 4888 | 0.00 |
| 21.393 | 32649 | 0.01 | 3566 | 0.00 |
| 21.687 | 47737 | 0.01 | 4852 | 0.00 |
| 21.980 | 56670 | 0.01 | 5955 | 0.00 |
| 22.277 | 21514 | 0.01 | 2151 | 0.00 |
| 22.600 | 14015 | 0.00 | 2185 | 0.00 |
| Total | 421827573 | 100.00 | 127026346 | 100.00 |

FIG. 5 Continued

Area Percent Report

Data file: D:\m-hexachloro\97-4-2
Method: E:\7820\method\hexachloro.met
Acquisition Time: 2012-8-22 14:22:08 (GMT +08:00)

| Rear Signal Result Retention time | Area | Area Percent | Peak Height | Peak Height Percent |
|---|---|---|---|---|
| 2.463 | 2239 | 0.00 | 512 | 0.00 |
| 2.903 | 85727 | 0.01 | 9973 | 0.01 |
| 3.210 | 24576 | 0.00 | 3679 | 0.00 |
| 3.337 | 3423 | 0.00 | 973 | 0.00 |
| 3.417 | 3250 | 0.00 | 820 | 0.00 |
| 3.657 | 5273 | 0.00 | 1408 | 0.00 |
| 3.737 | 2262 | 0.00 | 766 | 0.00 |
| 3.793 | 2343 | 0.00 | 798 | 0.00 |
| 4.033 | 336044 | 0.02 | 81953 | 0.05 |
| 4.303 | 278844 | 0.02 | 71408 | 0.04 |
| 4.623 | 1150 | 0.00 | 502 | 0.00 |
| 4.703 | 6039 | 0.00 | 2337 | 0.00 |
| 4.787 | 4791 | 0.00 | 1497 | 0.00 |
| 4.833 | 3403 | 0.00 | 1281 | 0.00 |
| 4.920 | 15633 | 0.00 | 4998 | 0.00 |
| 4.987 | 63902 | 0.00 | 22473 | 0.01 |
| 5.073 | 20396 | 0.00 | 4899 | 0.00 |
| 5.290 | 10639 | 0.00 | 1791 | 0.00 |
| 5.490 | 5812 | 0.00 | 1373 | 0.00 |
| 5.553 | 13878 | 0.00 | 4980 | 0.00 |
| 5.670 | 7218 | 0.00 | 2855 | 0.00 |
| 5.760 | 2678 | 0.00 | 750 | 0.00 |
| 5.893 | 8583 | 0.00 | 1845 | 0.00 |
| 6.097 | 49092 | 0.00 | 15838 | 0.01 |
| 6.243 | 9489 | 0.00 | 2425 | 0.00 |
| 6.477 | 3946 | 0.00 | 1709 | 0.00 |
| 6.590 | 1519345 | 0.09 | 633207 | 0.37 |
| 6.720 | 24658 | 0.00 | 6284 | 0.00 |

| | | | | |
|---|---|---|---|---|
| 6.893 | 28420 | 0.00 | 11101 | 0.01 |
| 6.970 | 1263385 | 0.08 | 444183 | 0.26 |
| 7.090 | 501222 | 0.03 | 166292 | 0.10 |
| 7.360 | 5792 | 0.00 | 1793 | 0.00 |
| 7.427 | 9143 | 0.00 | 3119 | 0.00 |
| 7.533 | 6746 | 0.00 | 1997 | 0.00 |
| 7.630 | 10565 | 0.00 | 5529 | 0.00 |
| 7.670 | 19854 | 0.00 | 7139 | 0.00 |
| 7.790 | 320850 | 0.02 | 101588 | 0.06 |
| 8.050 | 2315485 | 0.14 | 747298 | 0.43 |
| 8.300 | 5668775 | 0.35 | 936913 | 0.54 |
| 8.657 | 2557683 | 0.16 | 837561 | 0.48 |
| 8.750 | 6222271 | 0.39 | 830094 | 0.48 |
| 9.197 | 612366 | 0.04 | 160288 | 0.09 |
| 9.293 | 138313 | 0.01 | 43996 | 0.03 |
| 9.777 | 1429916869 | 88.93 | 113627056 | 65.66 |
| 9.843 | 526706 | 0.03 | 346962 | 0.20 |
| 9.910 | 2389395 | 0.15 | 1429584 | 0.83 |
| 9.997 | 916008 | 0.06 | 609308 | 0.35 |
| 10.180 | 8927302 | 0.56 | 4359464 | 2.52 |
| 10.287 | 9853 | 0.00 | 3883 | 0.00 |
| 10.373 | 147065 | 0.01 | 56229 | 0.03 |
| 10.483 | 116551 | 0.01 | 29584 | 0.02 |
| 10.660 | 75697 | 0.00 | 24117 | 0.01 |
| 10.813 | 67607991 | 4.20 | 18980208 | 10.97 |
| 10.853 | 3409601 | 0.21 | 2575426 | 1.49 |
| 10.910 | 75250 | 0.00 | 34639 | 0.02 |
| 11.020 | 80942 | 0.01 | 21573 | 0.01 |
| 11.123 | 1516819 | 0.09 | 577241 | 0.33 |
| 11.277 | 26679 | 0.00 | 5894 | 0.00 |
| 11.357 | 113155 | 0.01 | 27738 | 0.02 |
| 11.503 | 16413581 | 1.02 | 5464607 | 3.16 |
| 11.640 | 13148275 | 0.82 | 5213043 | 3.01 |
| 11.740 | 52524 | 0.00 | 13807 | 0.01 |
| 11.873 | 17490809 | 1.09 | 7138116 | 4.13 |
| 11.970 | 1144041 | 0.07 | 558414 | 0.32 |
| 12.107 | 151848 | 0.01 | 44991 | 0.03 |
| 12.277 | 5403525 | 0.34 | 2407281 | 1.39 |
| 12.407 | 56269 | 0.00 | 14233 | 0.01 |
| 12.473 | 83567 | 0.01 | 21266 | 0.01 |
| 12.593 | 1957313 | 0.12 | 892571 | 0.52 |
| 13.057 | 9820495 | 0.61 | 2664866 | 1.54 |
| 13.120 | 3335473 | 0.21 | 613578 | 0.35 |
| 13.340 | 81692 | 0.01 | 18739 | 0.01 |
| 13.493 | 22848 | 0.00 | 6803 | 0.00 |
| 13.553 | 15571 | 0.00 | 5309 | 0.00 |
| 13.633 | 26566 | 0.00 | 6076 | 0.00 |
| 13.727 | 30424 | 0.00 | 9204 | 0.01 |
| 13.803 | 12400 | 0.00 | 4625 | 0.00 |
| 19.837 | 275474 | 0.02 | 16480 | 0.01 |
| 20.550 | 115737 | 0.01 | 5935 | 0.00 |
| 20.693 | 26495 | 0.00 | 4242 | 0.00 |
| 20.960 | 135229 | 0.01 | 16734 | 0.01 |

FIG. 6 Continued

| | | | | |
|---|---|---|---|---|
| 21.167 | 8138 | 0.00 | 1461 | 0.00 |
| 21.417 | 13357 | 0.00 | 1703 | 0.00 |
| 22.043 | 33074 | 0.00 | 4077 | 0.00 |
| 22.623 | 26606 | 0.00 | 5127 | 0.00 |
| Total | 1607932717 | 100.00 | 173044419 | 100.00 |

FIG. 6 Continued

Area Percent Report

Data file: D:\m-hexachloro\105-5.dat
Method: E:\7820\method\hexachloro.met
Acquisition Time: 2012-9-17 23:50:48 (GMT +08:00)

| Rear Signal Result Retention time | Area | Area Percent | Peak Height | Peak Height Percent |
|---|---|---|---|---|
| 2.167 | 2872 | 0.00 | 2556 | 0.00 |
| 2.757 | 28165 | 0.01 | 15300 | 0.01 |
| 3.140 | 54069 | 0.01 | 28488 | 0.02 |
| 3.550 | 10384 | 0.00 | 6773 | 0.01 |
| 3.633 | 1339 | 0.00 | 443 | 0.00 |
| 3.993 | 1994 | 0.00 | 1111 | 0.00 |
| 4.173 | 22104 | 0.00 | 11137 | 0.01 |
| 4.660 | 4906 | 0.00 | 2441 | 0.00 |
| 4.890 | 26541 | 0.01 | 14059 | 0.01 |
| 4.943 | 1490 | 0.00 | 846 | 0.00 |
| 5.057 | 5328 | 0.00 | 1838 | 0.00 |
| 5.150 | 1748 | 0.00 | 792 | 0.00 |
| 5.207 | 20557 | 0.00 | 11655 | 0.01 |
| 5.300 | 1022 | 0.00 | 323 | 0.00 |
| 5.430 | 1198 | 0.00 | 285 | 0.00 |
| 5.553 | 3272 | 0.00 | 1677 | 0.00 |
| 5.707 | 3047 | 0.00 | 1244 | 0.00 |
| 5.780 | 1875 | 0.00 | 1002 | 0.00 |
| 5.873 | 18318 | 0.00 | 6814 | 0.01 |
| 5.947 | 10337 | 0.00 | 5451 | 0.00 |
| 6.040 | 12017 | 0.00 | 7021 | 0.01 |
| 6.173 | 3567 | 0.00 | 1301 | 0.00 |
| 6.477 | 20173 | 0.00 | 11395 | 0.01 |
| 6.583 | 36153 | 0.01 | 14263 | 0.01 |
| 6.663 | 1735 | 0.00 | 672 | 0.00 |
| 6.737 | 4914 | 0.00 | 1953 | 0.00 |
| 6.957 | 199479 | 0.04 | 112424 | 0.10 |
| 7.090 | 6480 | 0.00 | 2092 | 0.00 |

| | | | | |
|---|---|---|---|---|
| 7.227 | 31391 | 0.01 | 16266 | 0.01 |
| 7.413 | 8116 | 0.00 | 2509 | 0.00 |
| 7.537 | 47327 | 0.01 | 24518 | 0.02 |
| 7.673 | 8387 | 0.00 | 2696 | 0.00 |
| 7.817 | 135102 | 0.03 | 66166 | 0.06 |
| 7.977 | 204302 | 0.04 | 93289 | 0.08 |
| 8.050 | 43911 | 0.01 | 22185 | 0.02 |
| 8.107 | 2845 | 0.00 | 1394 | 0.00 |
| 8.293 | 3456327 | 0.69 | 1663619 | 1.44 |
| 8.433 | 80427 | 0.02 | 29146 | 0.03 |
| 8.613 | 369121 | 0.07 | 86919 | 0.08 |
| 8.747 | 1252967 | 0.25 | 484801 | 0.42 |
| 8.843 | 34096 | 0.01 | 8303 | 0.01 |
| 8.967 | 8345052 | 1.67 | 2616654 | 2.27 |
| 9.290 | 5793160 | 1.16 | 777103 | 0.67 |
| 9.570 | 351362178 | 70.12 | 52919596 | 45.91 |
| 9.647 | 11933 | 0.00 | 6292 | 0.01 |
| 9.753 | 33201085 | 6.63 | 14176809 | 12.30 |
| 9.813 | 430248 | 0.09 | 283810 | 0.25 |
| 9.870 | 188027 | 0.04 | 102493 | 0.09 |
| 9.953 | 6176203 | 1.23 | 3545880 | 3.08 |
| 10.057 | 173991 | 0.03 | 96341 | 0.08 |
| 10.120 | 463124 | 0.09 | 246612 | 0.21 |
| 10.177 | 28103 | 0.01 | 16765 | 0.01 |
| 10.230 | 2217 | 0.00 | 1188 | 0.00 |
| 10.360 | 11932730 | 2.38 | 5901842 | 5.12 |
| 10.423 | 2451586 | 0.49 | 1275116 | 1.11 |
| 10.490 | 134637 | 0.03 | 75753 | 0.07 |
| 10.650 | 1981721 | 0.40 | 713370 | 0.62 |
| 10.763 | 30667460 | 6.12 | 11646703 | 10.10 |
| 10.907 | 11474861 | 2.29 | 5509163 | 4.78 |
| 10.987 | 522820 | 0.10 | 237476 | 0.21 |
| 11.093 | 331675 | 0.07 | 164281 | 0.14 |
| 11.193 | 1101938 | 0.22 | 611260 | 0.53 |
| 11.337 | 1609598 | 0.32 | 822830 | 0.71 |
| 11.477 | 6337052 | 1.26 | 2206155 | 1.91 |
| 11.600 | 1311392 | 0.26 | 651982 | 0.57 |
| 11.650 | 212134 | 0.04 | 108054 | 0.09 |
| 11.743 | 967841 | 0.19 | 311838 | 0.27 |
| 11.843 | 5098652 | 1.02 | 2606690 | 2.26 |
| 11.900 | 68928 | 0.01 | 34166 | 0.03 |
| 11.977 | 980388 | 0.20 | 248213 | 0.22 |
| 12.113 | 3104388 | 0.62 | 1524216 | 1.32 |
| 12.190 | 293835 | 0.06 | 101699 | 0.09 |
| 12.267 | 1493859 | 0.30 | 659034 | 0.57 |
| 12.360 | 174637 | 0.03 | 40482 | 0.04 |
| 12.463 | 891049 | 0.18 | 331574 | 0.29 |
| 12.533 | 239660 | 0.05 | 106525 | 0.09 |
| 12.587 | 1555603 | 0.31 | 708381 | 0.61 |
| 12.653 | 187727 | 0.04 | 85477 | 0.07 |
| 12.710 | 99859 | 0.02 | 45476 | 0.04 |
| 12.773 | 233562 | 0.05 | 65794 | 0.06 |
| 12.850 | 313795 | 0.06 | 96985 | 0.08 |

FIG. 7 Continued

| | | | | |
|---|---|---|---|---|
| 12.910 | 235652 | 0.05 | 82229 | 0.07 |
| 12.997 | 1615637 | 0.32 | 416275 | 0.36 |
| 13.117 | 138862 | 0.03 | 56224 | 0.05 |
| 13.163 | 191606 | 0.04 | 52695 | 0.05 |
| 13.240 | 244146 | 0.05 | 83372 | 0.07 |
| 13.353 | 74204 | 0.01 | 18880 | 0.02 |
| 13.457 | 114463 | 0.02 | 39178 | 0.03 |
| 13.500 | 109785 | 0.02 | 36747 | 0.03 |
| 13.620 | 100385 | 0.02 | 22200 | 0.02 |
| 13.673 | 28270 | 0.01 | 10487 | 0.01 |
| 13.750 | 63032 | 0.01 | 11001 | 0.01 |
| 13.990 | 2131 | 0.00 | 1453 | 0.00 |
| 22.633 | 8935 | 0.00 | 1442 | 0.00 |
| Total | 501055219 | 100.00 | 115279428 | 100.00 |

FIG. 7 Continued

METHOD FOR THE PREPARATION OF TRICHLOROMETHYL-GROUP-SUBSTITUTED BENZENE

CROSS-REFERENCE TO RELATED APPLICATIONS

The subject application is a U.S. national stage of PCT/CN2014/086372 filed on Sep. 12, 2014 and claims priority on Chinese application nos. 201310422286.8 filed on Sep. 13, 2013 and 201420373955.7 filed on Jul. 8, 2014. The contents and subject matter of the PCT and Chinese priority applications are incorporated herein by reference.

TECHNICAL FIELD

The present application relates to a method for photochlorination, and specifically to photochlorination by a photochemical reaction of an aromatic compound with gaseous chlorine so as to prepare a trichloromethyl-substituted benzene, and to a method using bis-(trichloromethyl)-benzene as the trichloromethyl-substituted benzene to prepare by further reaction bis-(chloroformyl)-benzene. Through the control of temperature, illuminance and consumption of gaseous chlorine, the method of this application can greatly improve the purity of trichloromethyl-substituted benzene and further prepare polymer-grade bis-(chloroformyl)-benzene with low cost. The present application also relates to a method for purifying trichloromethyl-substituted benzene, and specifically to a method for purifying trichloromethyl-substituted benzene via molecular distillation. The present application further relates to a photochlorination reactor for use in photochlorination reactions (such as those of the present application).

BACKGROUND

The photochlorination reactions use photons to initiate chlorination of pendant free radicals. In some reactions, a free radical photoinitiator is used alone or in combination with a free radical thermal initiator to form a composite initiation system. Sometimes, a second component and even a third component may be added to prevent chlorine substitution on the benzene ring as side-reaction. Generally, a mercury lamp is used as a light source. Because purity of trichloromethyl-substituted benzene is not ideal, there is great difficulty using this technique to realize industrial mass production.

The present inventors have recognized that the method of preparing trichloromethyl-substituted benzene via photochlorination in the prior art has drawbacks in the following ways.

1) The photochlorination reaction is a radical chain reaction and due to the side-reaction, chlorination site and chlorination depth are relatively difficult to control. In order to separate complex photochlorination products, a great number of rectification operations have to be performed in DE3146868 and JP 57-130931, which greatly increases the production cost of such products. To prevent chlorine substitution on the benzene ring, sulfur and acetyl chloride are added in U.S. Pat. No. 1,345,373, a metal carbonate is added in U.S. Pat. No. 1,384,909, phosphor and sulfur are added in U.S. Pat. No. 1,733,268, an organic base is added in U.S. Pat. No. 2,034,962, an amide is added in U.S. Pat. No. 2,695,873, amines are used in U.S. Pat. No. 2,817,632 and U.S. Pat. No. 2,844,635, and triphenyl phosphine is used in U.S. Pat. No. 3,363,013. These additional components unavoidably affect the purity and subsequent purification of trichloromethyl-substituted benzene. It is reported in U.S. Pat. No. 4,029,560 and U.S. Pat. No. 4,048,033 that in the chlorination, the target product is used as solvent to inhibit chlorine substitution on the benzene ring as side-reaction, and for example, in the chlorination of 1,3-dimethylbenzene, 1,3-bis-(trichloromethyl)-benzene is used as solvent, which requires a great amount of 1,3-bis-(trichloromethyl)-benzene to be used repeatedly. Thus, this method has complex process and high cost.

In summary, in order to achieve chlorination of all hydrogen atoms on pendant methyl groups without chlorination of hydrogen atoms on the benzene ring in the prior art, multiple adjuvant components need to be introduced, which will 'contaminate' the target product trichloromethyl-substituted benzene and thus are not suitable for preparation of high-purity products.

2) A free radical initiator is also required to initiate the photochlorination reaction.

Wang Lumin et al. (Journal of Tonghua Normal University, 2005, 26(4):46-47) have found that a free radical initiator is required to maintain the reaction for the photochlorination of 1,3-dimethylbenzene.

A method of preparing tetrachloro-o-xylene from o-xylene via photochlorination in three temperature stages is disclosed in CN102211975A. In this method, the photochlorination includes three temperature stages of 120-125° C., 125-130° C. and 130-135° C., which correspond to the amounts of chlorine introduced of ⅓, ½ and ⅙ of the total amount of chlorine, respectively. Similarly, benzoyl peroxide is added as a light sensitive catalyst in this reaction. After this reaction in the three temperature stages is completed, the yield of tetrachloro-o-xylene is only 65% and the yield of pentachloro-o-xylene is 10%. Because of the addition of the light sensitive catalyst in this reaction, the purity of the resulting tetrachloro-o-xylene only reaches 90% even in case of further purification.

3) A mercury lamp is generally used as a light source in a photochlorination reaction. However, the said light source has numerous disadvantages.

The present inventors have found that the short-wavelength light of a low-pressure mercury lamp can bring out other photochemical side reactions, resulting in decreased product purity, and the long wavelength light of a high-pressure or medium-pressure mercury lamp is not sufficient to give rise to a chlorine radical reaction, resulting in increased energy consumption. In addition, more heat is generated when a mercury lamp is used as a light source; and thus it is necessary to provide a corresponding cooling device, making the reactor structure complicated.

It is disclosed in CN1948245 that a light emitting diode (LED) having a wavelength range of 300-600 nm and a power range of 0.1 W-1000 W is used as a light source in a photochlorination reaction to produce benzyl chloride, where the reaction temperature is maintained at 90-150° C. It is recorded in the document that its technical problem to be solved is to provide a photochlorination method with low power consumption and low heat generation from the light source; and the utilization rate of the light source can be improved by selecting the light emitting diode as the light source. Although this document mentioned that m-dimethylbenzene may be used as a raw material, all the examples of this document do not disclose the purity and the yield of the product.

The applicant has also found that the illuminance of the light source for this reaction is not researched by the prior art.

In addition, bis-(trichloromethyl)-benzene in trichloromethyl-substituted benzene can react with water or phthalic acid to prepare an intermediate of aramid fiber, bis-(chloroformyl)-benzene. For producing aramid fiber, a high purity of bis-(chloroformyl)-benzene is needed as a starting material, otherwise the quality of aramid fiber is difficult to meet the specified requirements. Further, relevant research on the purification of bis-(trichloromethyl)-benzene has been performed by the applicant. In conventional processes, such as distillation and rectification under atmospheric pressure, separation and purification are achieved depending on the different boiling points of compounds, and it is required to remain in a high-temperature environment for a long time. In this case, partial polymerization will be generated. Thus, use of such purification processes leads to coke formation, causing damage to the apparatus which then needs to be periodically cleaned. On the other hand, the coke is harmful to the environment and needs to be properly handled, resulting in high environmental cost. For vacuum rectification, although the temperature required for separation can be reduced, the material to be separated must be maintained at a certain level in a re-boiler to generate a static pressure difference, so that the vaporizing temperature of the material in a column reactor is increased, and thus thermal decomposition of the material may be difficult to avoid in some cases. The presence of inert gases is beneficial to rectification of the heat sensitive material, but it causes problems in condensation or cooling. For recrystallization process, consumption of a substantial amount of solvent is required, which causes pollution to the environment, and impurity carried by the solvent contaminates the product.

Among the preparation methods of bis-(chloroformyl)-benzene in the prior art, the thionyl chloride method with phthalic acid as a raw material is most commonly used (for example, see CN 102516060A, CN 102344362A). However, in the process, phthalic acid having a high purity of 99.99% is required to obtain desired bis-(chloroformyl)-benzene, which results in a significant increase in the preparation cost and is a more difficult process.

In addition, relevant research on the apparatuses for photochlorination reaction has been performed by the applicant. Photochlorination reactors are widely used in the field of chemical production. Most of the existing apparatuses for photochlorination reaction compose three parts, a reactor, a light source, and jacketed condenser. For example, the photochlorination reactors disclosed in patents CN200942338Y and CN101456788B are essentially equivalent and both include a cooling jacket outside a cylinder, an anti-corrosion material lining the cylinder, a sprayer, and light sources arranged at angles. However, in the two photochlorination reactors, desired increase in illumination intensity and range is not achieved, and uneven illumination distribution exists in the reactors, which easily causes side reactions in the photochlorination. In addition, in the disclosed technological solutions, both ends of tubes in which the light sources are placed extends through the reactor cylinder; so that in actual production process, when the reaction temperature is higher, uneven heating of the tubes may easily be caused, resulting in damage to the tubes.

SUMMARY OF THE INVENTION

In order to overcome the abovementioned shortcomings, the inventors have completed this application. This application provides a method for producing a high purity of trichloromethyl-substituted benzene. The resulting product by the present method can be subsequently purified in a simple and low-cost procedure, which enables the present method to be industrialized. In addition, the present invention provides the preparation of bis-(chloroformyl)-benzene with a high purity, which is useful for producing aramid fiber, where a high purity of bis-(trichloromethyl)-benzene in trichloromethyl-substituted benzene is used as a raw material to react with 99.5% phthalic acid, and then bis-(chloroformyl)-benzene with a high purity is obtained following purification such as rectification or molecular distillation. The present application enables the production cost of bis-(chloroformyl)-benzene to be significantly reduced. The present application further provides a method for purifying trichloromethyl-substituted benzene, particularly bis-(trichloromethyl)-benzene. In addition, the present application further provides a photochlorination reactor with enhanced illumination intensity and range, and a more evened illumination distribution.

In one aspect, the present invention relates to a photochemical method for intermittently or continuously preparing trichloromethyl-substituted benzene, characterized in that an aromatic compound of formula $(X)_a C_6 H_{6-a-b}(CH_3)_b$ or a pendant alkyl chloride thereof as a raw material is reacted with chlorine under illumination conditions to prepare trichloromethyl-substituted benzene, where the illumination has a light source wavelength within about 350 nm to 700 nm and a wavelength amplitude within no more than about 200 nm, and where chlorine feeding is initiated under conditions of a starting reaction temperature within about 0° C. to 85° C. and a starting illuminance within about 2000 Lux to about 55000 Lux, for a first reaction stage where the reaction temperature is controlled to no higher than about 120° C. under the illuminance; and then the remaining amount of chlorine is fed at a higher reaction temperature and/or under higher illuminance until the reaction is completed; where X is a chlorine, bromine or fluorine atom, "a" is an integer selected from 0, 1, 2, 3, 4 and 5, "b" is an integer selected from 1, 2, 3 and 4, and a+b≤6.

Further, when "a" is 0 and "b" is 2, a high purity bis-(trichloromethyl)-benzene obtained by the method of the present invention can be used for preparing a high purity bis-(chloroformyl)-benzene. The high purity of bis-(chloroformyl)-benzene can be used as a raw material of aramid fiber. The method of the present application greatly reduces the cost in preparation of bis-(chloroformyl)-benzene with a high purity.

Further, the present application relates to a method for preparing bis-(chloroformyl)-benzene, comprising the steps of: a) preparing bis-(trichloromethyl)-benzene by any of the methods of the present application; b) reacting bis-(trichloromethyl)-benzene in step a) to prepare bis-(chloroformyl)-benzene. In step b), bis-(trichloromethyl)-benzene is preferably reacted with water or phthalic acid, more preferably with phthalic acid.

In another aspect, the present application relates to a method for preparing bis-(chloroformyl)-benzene, comprising reacting bis-(trichloromethyl)-benzene with a purity of above 99% and preferably above 99.2% with industrial-grade phthalic acid with a purity of 99.5%.

In an additional aspect, the present application relates to a method for purifying trichloromethyl-substituted benzene (for example, bis-(trichloromethyl)-benzene) via molecular distillation, comprising the steps of:

(1) pre-treating a crude trichloromethyl-substituted benzene (for example, bis-(trichloromethyl)-benzene) to remove light components therein;

(2) subjecting trichloromethyl-substituted benzene (for example, bis-(trichloromethyl)-benzene) pre-treated in step (1) to separation by distillation in a primary molecular distiller at a controlled molecular distillation temperature of from 75 to 135° C. and absolute pressure of from 3 Pa to 90 Pa, to give a distillate and a residue; and (3) collecting and optionally purifying the distillate in step (2), to obtain purified trichloromethyl-substituted benzene (for example, bis-(trichloromethyl)-benzene).

The pre-treatment in step (1) of the molecular distillation method of the present invention is one of thin film evaporation, distillation or rectification. In an embodiment of the molecular distillation method of the present invention, in step (2), the residue in the primary molecular distiller is subjected to a secondary or multiple-stage molecular distillation as needed, to give distillates and residues therefrom; and accordingly, in step (3), the distillates of the stages in step (2) are collected and combined and optionally purified, to give purified trichloromethyl-substituted benzene (for example, bis-(trichloromethyl)-benzene).

In an embodiment of the molecular distillation method of the present invention, trichloromethyl-substituted benzene (for example, bis-(trichloromethyl)-benzene) is pre-treated using thin film evaporation at a temperature of from 90° C. to 150° C. and a vacuum degree of from 0.080 MPa to 0.098 MPa.

In still another aspect, the present application relates to a photochlorination reactor comprising a reactor cylinder (simply referred as cylinder) and a transparent tube (simply referred as tubes) for placing a light source therein, fixed on the cylinder, characterized in that when the cylinder is transparent, a reflecting layer is disposed on an outer wall of the cylinder; when the cylinder is not transparent, a reflecting layer is disposed on an inner wall of the cylinder; when the tube has a closed end and an open end, the closed end is located in the reactor cylinder and the open end faces outward and radially extends through the reactor cylinder; and when the tube has two open ends, both ends radially extend through the reactor cylinder. The reactor of the present application can be used in the photochemical method for preparing trichloromethyl-substituted benzene of the present application.

DETAILED DESCRIPTION OF THE INVENTION

Figure 1:
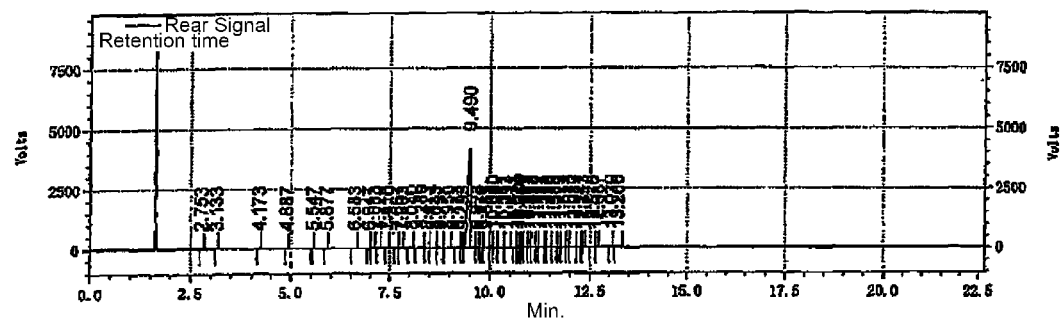
FIG. 1 is a gas chromatogram of the reaction product of example 1.
Figure 2:
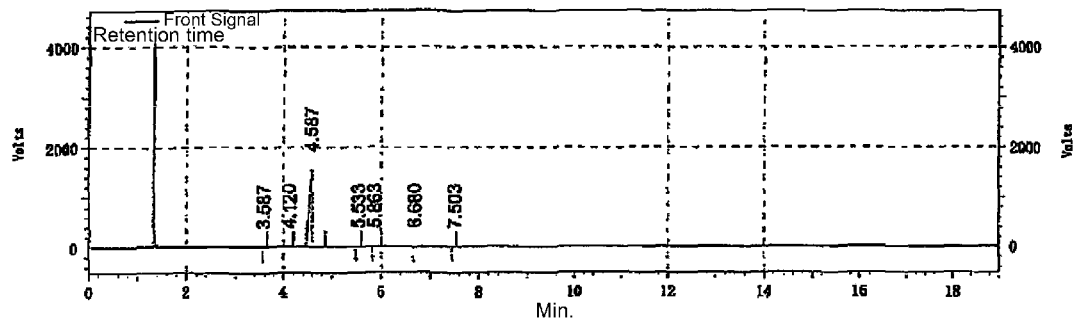
FIG. 2 is a gas chromatogram of the reaction product of example 9.
Figure 3:
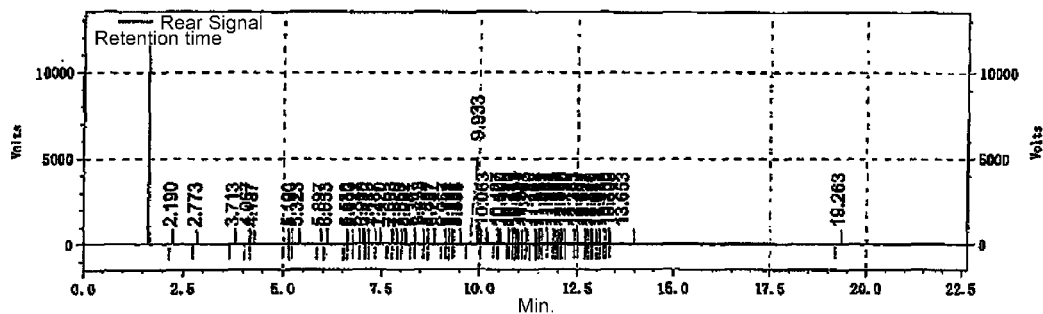
FIG. 3 is a gas chromatogram of the reaction product of example 12.
Figure 4:
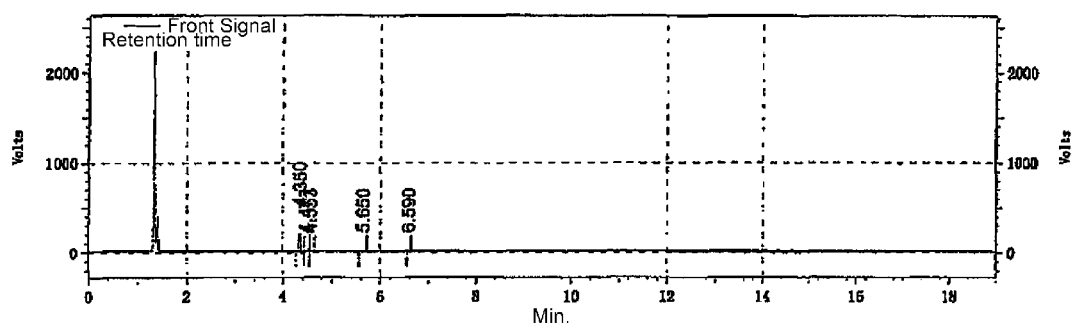
FIG. 4 is a gas chromatogram of the reaction product of example 18.
Figure 5:
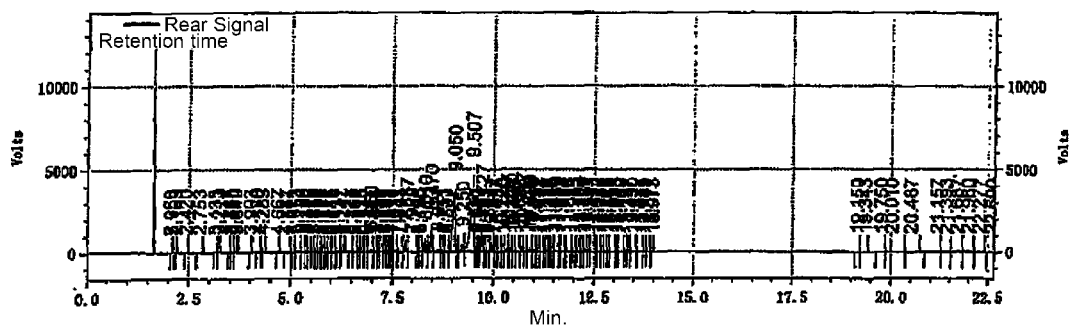
FIG. 5 is a gas chromatogram of the reaction product of example 21.
Figure 6:
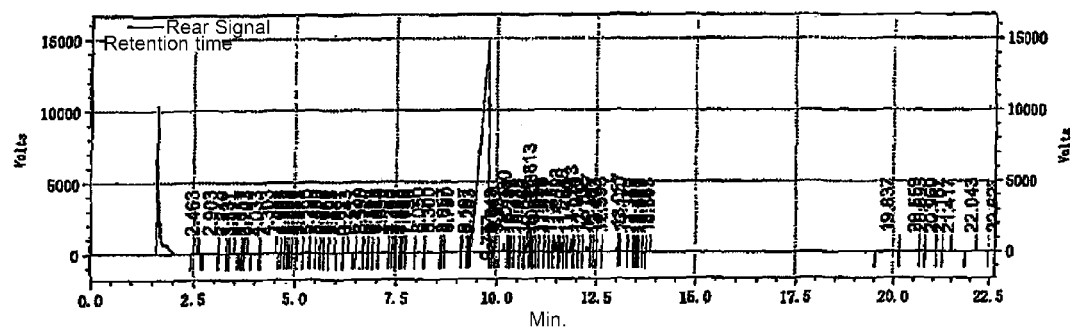
FIG. 6 is a gas chromatogram of the reaction product of example 22.
Figure 7:
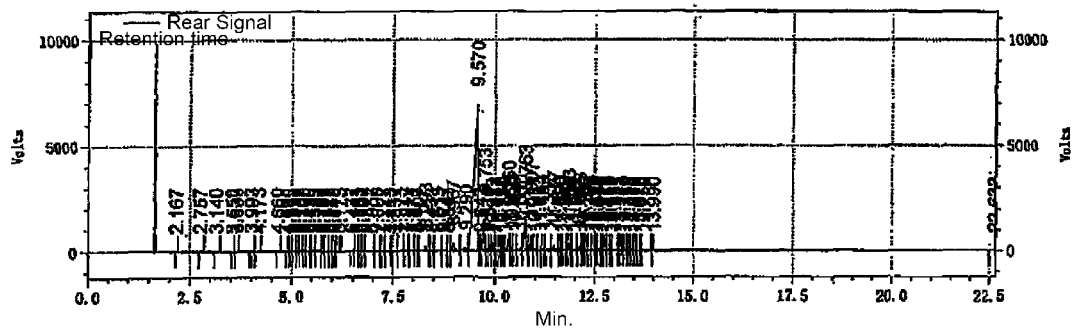
FIG. 7 is a gas chromatogram of the reaction product of example 27.

In the existing methods in the prior art for preparing trichloromethyl-substituted benzene by photochlorination, in addition to the target product, the resulting product comprises a number of side products that are difficult to separate from the target product. Multiple rectification operations are required in order to remove these side products that are difficult to separate. This makes the methods for preparing trichloromethyl-substituted benzene in the prior art expensive, which is a main reason as to why the methods are not used in industry for large-scale production of bis-(trichloromethyl)-benzene.

The inventors have found through research that the side products that are difficult to separate in the photochlorination methods in the prior art are concentrated in light components in the rectification operations. Through research, the inventors have found that these side products as light components mainly result from chlorination on the benzene ring, for example mono-chlorination on the benzene ring with tetra-chlorination or penta-chlorination on the pendant methyl groups. These side products from chlorination on the benzene ring have boiling points close to that of bis-(trichloromethyl)-benzene, and thus multiple rectification operations with a high cost are required in the separation process.

Also, the present inventors have innovatively found that in the photochemical reaction, the side products from chlorination on the benzene ring can be greatly reduced in the preparation of trichloromethyl-substituted benzene, by reacting an aromatic compound with a controlled amount of chlorine at a certain temperature and luminance in a first reaction stage.

Accordingly, in one aspect, the present invention relates to a photochemical method for intermittently or continuously preparing trichloromethyl-substituted benzene, characterized in that an aromatic compound of formula $(X)_a C_6 H_{6-a-b} (CH_3)_b$ or a pendant alkyl chloride thereof as a raw material is reacted with chlorine under illumination conditions to prepare trichloromethyl-substituted benzene, where the illumination has a light source wavelength within the range of about 350 nm to about 700 nm and a wavelength amplitude within no more than about 200 nm, and where chlorine feeding is initiated under conditions of a starting reaction temperature within the range of about 0° C. to 85° C. and a starting illuminance within the range of about 2000 Lux to about 55000 Lux, for a first reaction stage where the reaction temperature is controlled to no higher than about 120° C. under the illuminance; and then the remaining amount of chlorine is fed at a higher reaction temperature and/or under higher illuminance until the reaction is completed; where X is a chlorine, bromine or fluorine atom, "a" is an integer selected from 0, 1, 2, 3, 4 and 5, "b" is an integer selected from 1, 2, 3 and 4, and a+b≤6. In a preferred aspect of the method, the light source preferably is an LED lamp.

The present inventors have found that it is quite necessary to control the starting reaction temperature and illuminance in the first reaction stage for obtaining a reaction mixture with a high purity (before purification). In particular, by performing the reaction for the first reaction stage following the conditions described above, the side products from chlorination on the benzene ring can be greatly reduced without strictly controlling later reaction conditions, as long as the reaction temperature and/or illuminance is increased with the depth of chlorination. In addition, where the reaction conditions for the first reaction stage are strictly controlled, even if the target product in the reaction mixture has a low purity value after the reaction is completed, due to the characteristics of this process, in some embodiments, the chlorination reaction mixture with a low purity can be easily purified by conventional methods, for example, a single rectification or molecular distillation, to reach a product purity of above 99%.

The method of the present invention may be performed in an intermittent or continuous process. In the continuous process, for the ease of operation, the temperature, illuminance, wavelength amplitude or light source wavelength may independently vary within particular ranges.

The minimum extent or duration of the first reaction stage may be determined depending on the particular reaction system by simple experimentation, so as to control the amount of impurities in the final reaction mixture or the purity of target product trichloromethyl-substituted benzene. There is no particular limit for the maximum extent or duration of the first reaction stage. In the initial stage of the chlorination reaction, due to exothermic reaction, it is necessary to control the feeding speed of chlorine so as to keep the reaction temperature below 120° C. However, as the chlorination reaction proceeds and the depth of chlorination increases, the reaction speed under the conditions for the first reaction stage is slower, so that it is necessary to raise the temperature and/or illuminance to reach a rational or economically feasible reaction speed. Therefore, in the later period of the first reaction stage, the temperature and/or illuminance should be increased.

The present inventors have found that, in the first reaction stage, it is advantageous to consume preferably at least about ⅙ of a total amount of chlorine required by the reaction before increasing the temperature and illuminance. In some preferred aspects of the present invention, greater than or equal to about ⅙, ⅕, ¼, ⅓, ⅖ or ½ of a total required amount of chlorine by the reaction is consumed in the first reaction stage before increasing the temperature and illuminance. In some preferred aspects of the present invention, between about ⅙ and ⅕, ⅙ and ¼, ⅙ and ⅓, ⅙ and ⅖, ⅙ and ½, ⅕ and ¼, ⅕ and ⅓, ⅕ and ⅖, ⅕ and ½, ¼ and ⅓, ¼ and ⅖, ¼ and ½, ⅓ and ⅖, ⅓ and ½ or ⅖ and ½ of a total required amount of chlorine by the reaction is consumed in the first reaction stage before increasing the temperature and illuminance.

In some preferred aspects of the present invention, the illuminance in the first reaction stage may also be suitably adjusted. In some preferred aspects of the present invention, the illuminance in the first reaction stage is preferably between about 2000 Lux and about 10000 Lux, between about 2000 Lux and about 20000 Lux, between about 2000 Lux and about 30000 Lux, between about 2000 Lux and about 40000 Lux, between about 2000 Lux and about 50000 Lux, between about 2000 Lux and about 55000 Lux, between about 5000 Lux and about 10000 Lux, between about 5000 Lux and about 20000 Lux, between about 5000 Lux and about 30000 Lux, between about 5000 Lux and about 40000 Lux, between about 5000 Lux and about 50000 Lux, between about 5000 Lux and about 55000 Lux, between about 10000 Lux and about 20000 Lux, between about 10000 Lux and about 30000 Lux, between about 10000 Lux and about 40000 Lux, between about 10000 Lux and about 50000 Lux, between about 10000 Lux and about 55000 Lux, between about 15000 Lux and about 20000 Lux, between about 15000 Lux and about 30000 Lux, between about 15000 Lux and about 40000 Lux, between about 15000 Lux and about 50000 Lux, between about 15000 Lux and about 55000 Lux, between about 20000 Lux and about 25000 Lux, between about 20000 Lux and about 30000 Lux, between about 20000 Lux and about 35000 Lux, between about 20000 Lux and about 40000 Lux, between about 20000 Lux and about 45000 Lux, between about 20000 Lux and about 50000 Lux, between about 20000 Lux and about 55000 Lux, between about 25000 Lux and about 30000 Lux, between about 25000 Lux and about 35000 Lux, between about 25000 Lux and about 40000 Lux, between about 25000 Lux and about 45000 Lux, between about 25000 Lux and about 50000 Lux, between about 25000 Lux and about 55000 Lux, between about 30000 Lux and about 35000 Lux, between about 30000 Lux and about 40000 Lux, between about 30000 Lux and about 45000 Lux, between about 30000 Lux and about 50000 Lux, between about 30000 Lux-about 55000 Lux, between about 35000 Lux and about 40000 Lux, between about 35000 Lux and about 45000 Lux, between about 35000 Lux and about 50000 Lux, between about 35000 Lux and about 55000 Lux, between about 40000 Lux and about 45000 Lux, between about 40000 Lux and about 50000 Lux, between about 40000 Lux and about 55000 Lux, between about 45000 Lux and about 50000 Lux, between about 45000 Lux and about 55000 Lux, or between about 50000 Lux and about 55000 Lux. The inventors have found that it is critical for the present invention to control the first reaction stage to be performed in the manner described above. After the first reaction stage at the given temperature and luminance, the effect of temperature, illuminance and chlorine feed amount on the reaction results mainly relates to the reaction time in subsequent reaction stages such as second, third reaction stages.

In some preferred aspects of the present invention, the reaction temperature in the first reaction stage may also be properly adjusted. In some preferred aspects of the present invention, the reaction temperature in the first reaction stage is preferably between about 0° C. and about 10° C., between about 0° C. and about 20° C., between about 0° C. and about 30° C., between about 0° C. and about 40° C., between about 0° C. and about 55° C., between about 0° C. and about 60° C., between about 0° C. and about 70° C., between about 0° C. and about 80° C., between about 0° C. and about 85° C., between about 10° C. and about 20° C., between about 10° C. and about 30° C., between about 10° C. and about 40° C., between about 10° C. and about 50° C., between about 10° C. and about 55° C., between about 10° C. and about 60° C., between about 10° C. and about 70° C., between about 10° C. and about 80° C., between about 10° C. and about 85° C., between about 20° C. and about 30° C., between about 20° C. and about 40° C., between about 20° C. and about 50° C., between about 20° C. and about 55° C., between about 20° C. and about 60° C., between about 70° C. and about 55° C., between about 20° C. and about 80° C., between about 20° C. and about 85° C., between about 30° C. and about 40° C., between about 30° C. and about 50° C., between about 30° C. and about 55° C., between about 30° C. and about 60° C., between about 30° C. and about 70° C., between about 30° C. and about 80° C., between about 30° C. and about 85° C., between about 40° C. and about 55° C., between about 40° C. and about 60° C., between about 40° C. and about 70° C., between about 40° C. and about 80° C., between about 40° C. and about 85° C., between about 55° C. and about 60° C., between about 55° C. and about 65° C., between about 55° C. and about 70° C., between about 55° C. and about 75° C., between about 55° C. and about 80° C., between about 55° C. and about 85° C., between about 60° C. and about 65° C., between about 60° C. and about 70° C., between about 60° C. and about 75° C., between about 60° C. and about 80° C., between about 60° C. and about 85° C., between about 65° C. and about 70° C., between about 65° C. and about 75° C., between about 65° C. and about 80° C., between about 65° C. and about 85° C., between about 70° C. and about 75° C., between about 70° C. and about 70° C., between about 70°

C. and about 85° C., between about 75° C. and about 80° C., between about 75° C. and about 85° C., or between about 80° C. and about 85° C. In some preferred aspects of the present invention, the reaction temperature in the first reaction stage is preferably at about 55° C., about 60° C., about 65° C., about 70° C., about 75° C., about 80° C., or at about 85° C.

Preferably, in another aspect of the present application, in the process following the first reaction stage, the remaining amount of chlorine is fed at any temperature greater than the starting temperature of 120° C. (preferably no higher than about 350° C.) and any illuminance within the range of about 10000 Lux to about 100000 Lux greater than that in the first reaction stage. The process following the first reaction stage according to the method of the present application may be a single reaction stage or divided into several reaction stages such as two, three, four, five, six, seven, eight, nine or ten reaction stages. In the process following the first reaction stage, the illuminance is optionally increased when the temperature is increased in each stage. The present inventors have found that the reaction conditions in the process following the first reaction stage are flexible and may be selected as needed. The adjustment of varying temperature and illuminance in the process following the first reaction stage is primarily intended to facilitate the completion of the reaction. The inventors have found that on the basis of strictly controlling the first reaction stage according to the present invention, the variation in reaction conditions in the process following the first reaction stage has less influence on the purity of the final product.

Preferably, the process following the first reaction stage in the photochlorination reaction of the present invention may be further divided into a second and a third reaction stage. In the second reaction stage, the reaction temperature is controlled to be in the range of about 120 to about 160° C., the incoming illuminance is within the range of about 10000 to about 70000 Lux and greater than what is actually used in the first reaction stage, and ¼-⅖ of the total required amount of chlorine is fed. In the third reaction stage, the temperature is controlled to be greater than about 160° C. (preferably no higher than about 350° C.), the incoming illuminance is within the range of about 50000 to about 100000 Lux, greater than the illuminance that is actually used in the second reaction stage, and the remaining amount of chlorine is fed. In the second and third reaction stages, increasing the temperature and increasing the illuminance may be performed in any order.

For the conditions in all the stages in the photochlorination of an aromatic compound, both reaction temperature and illuminance are increasing from one stage to the next stage. Although some overlapping in illuminance ranges between various stages of the present invention exists, those skilled in the art can understand that the temperature and illuminance actually used in the second reaction stage are within the stated ranges and are higher than those in the first reaction stage; the temperature and illuminance actually used in the third reaction stage are within the stated ranges and are higher than those in the second reaction stage, and so on.

The present inventors also have found that it is critical for the present invention to control the first reaction stage to be performed in the manner described above. After the first reaction stage at the given temperature and luminance, the effect of temperature, illuminance and chlorine feed amount on the reaction results mainly relates to the reaction time in subsequent reaction stages such as the second and the third reaction stages. The combination of varying temperature and illuminance in subsequent reaction stages such as the second and the third reaction stages may obviously prolong or shorten the reaction time, following the first reaction stage, but will not significantly change such values, such as the purity of the chlorination product. For example, following the first reaction stage, when the temperature in the second and third reaction stages is maintained between 120° C. and 130° C., even if the illuminance is increased to 70000 Lux, the reaction cannot be completely performed; on the basis of the illuminance of 70000 Lux, when the temperature is increased to 140° C., the reaction can be completed in about 30 h; and when the temperature is further increased to 180° C., the reaction time is reduced from about 30 h to about 10 h. Additionally, when the second, third reaction stages are controlled at a temperature of 160° C., under conditions having an illuminance between 30000 and 40000 Lux, the reaction cannot be completely performed; on the basis of the temperature of 160° C., when the illuminance is increased to 50000 Lux, the reaction can be completed in about 36 h; and when the illuminance is further increased to 90000 Lux, the reaction time is reduced from about 36 h to about 10 h.

There is no particular requirement for the order of adjustment in temperature and illuminance in the second and third reaction stages for the reaction of the present invention. For example, the temperature may be first adjusted or the illuminance may be first adjusted; and the feeding of chlorine may be simultaneously performed with the adjustment of temperature or illuminance or may be separately performed. The reaction following the first reaction stage of the present application may be performed under the condition of feeding chlorine at a constant rate while gradually increasing the temperature and illuminance.

The expression 'chlorine feeding is initiated' herein means that the amount of chlorine in the reaction system is controlled to no more than 5% of the total required amount of chlorine before the temperature of the reaction system is adjusted to the range of 0° C.-85° C. In a preferred initial state, the amount of chlorine in the reaction system is controlled to no more than 4%, 3%, 2%, 1%, 0.5% or 0.1% of the total required amount of chlorine before the temperature of the reaction system is adjusted to the range of 0° C.-85° C. In a most preferred initial state, essentially no chlorine is fed and no chlorine is contained in the reaction system before the temperature of the reaction system is adjusted to the range of 0° C.-85° C.

The expression 'total required amount of chlorine by the reaction' herein means the amount of chlorine required for complete chlorination of hydrogen atoms on pendant alkyl groups in an aromatic compound, which is at least a theoretical molar amount for chlorination of the raw material aromatic compound. Taking xylene as an example, the total amount of chlorine in the method of the present invention is a molar amount that is above six times the number of moles of xylene. The excess amount of chlorine may be conventionally determined. Preferably, for saving the reaction time, fed amounts of chlorine in the respective stages herein may be adjusted depending on the monitored reaction results.

The inventors have found that the use of a light source with a particular wavelength amplitude has additional advantages in reducing the amount of side products in the photochlorination of xylene. In some embodiments, the light source used in the present application is preferably an LED lamp. The LED light source used in the present application has a peak wavelength ranging from 350 nm to 700 nm, preferably from 350 nm to 490 nm or preferably from 460 nm to 490 nm; and the peak wavelength of the LED light source in the present application may be, for example, 265 nm, 280 nm, 310 nm, from 360 to 365 nm, from 365 to 370 nm, from 375 to 380 nm, from 385 to 390 nm, or from 405 to 410 nm. The wavelength amplitude of the LED light source in the present application may be no more than 200 nm, preferably no more than 100 nm, preferably no more than 50 nm, preferably no more than 30 nm, and most preferably no more than 10 nm. In the present application, the LED light source may be made up of multiple point light sources, with a total power of 15 W, 30 W, 45 W, 60 W, 75 W, 90 W or the like. The LED light source in the present application may preferably be a 410-470 nm blue LED lamp, a 586-596 nm yellow LED lamp, or a 502-574 nm green LED lamp. In some embodiments, the light source used in the present application is more preferably a 460-490 nm blue LED lamp. In some embodiments, the light source used in the present application has a wavelength amplitude of no more than about 50 nm, preferably between about 10 and about 30 nm, more preferably between about 10 and about 25 nm.

The term 'wavelength amplitude' in the present application means the wavelength range at half peak height of light emission by the light source, not the peak wavelength of light. For example, a wavelength amplitude of 50 nm means that the wavelength range at half peak height of light emission by the light source is no more than 50 nm. The peak wavelength of the LED light source in the present application may vary from 350 nm to 700 nm, and for any given wavelength, the light source of incident light in the present application enables the wavelength amplitude to be controlled within 50 nm, for example wavelength amplitude 50 nm at peak wavelength of 465 nm, wavelength amplitude 50 nm at peak wavelength of 360 nm, wavelength amplitude 50 nm at peak wavelength of 586 nm. The present inventors have found that the LED light source also has the advantage of less heat generation, and thus the cost of the manufacturing equipment can be reduced, for example no additional cooling device is needed. In contrast, for the photochlorination reaction using a high-pressure mercury lamp as a light source, a corresponding cooling device is required (for example, see U.S. Pat. No. 5,514,254).

The illuminance in the present application may be determined by a conventional instrument such as illuminometer in the art. The wavelength in the present application may be determined by a conventional instrument such as monochromator in the art.

The meaning of the term 'about' in the present application can be defined as following: with respect to temperature, positive or negative variation of a stated value is no more than 2.5° C. (expressed as the stated value±2.5° C.), preferably the stated value±2.5° C., ±2° C. or ±1° C.; with respect to illuminance, positive or negative variation of a stated value is no more than 2500 Lux (expressed as the stated value±2500 Lux), preferably the stated value±2500 Lux, ±2000 Lux, ±1500 Lux, ±1000 Lux, ±500 Lux, ±200 Lux or ±100 Lux; with respect to wavelength, positive or negative variation of a stated value is no more than 5 nm (expressed as the stated value ±5 nm), preferably the stated value±4 nm, ±3 nm or ±1 nm; and with respect to wavelength amplitude, positive or negative variation of a stated value is no more than 3 nm (expressed as the stated value±3 nm), preferably the stated value±2 nm or ±1 nm.

The term 'pendant alkyl chloride' in the present application means a compound where hydrogen atoms on the alkyl groups in the aromatic compound are not completely substituted by the chlorine atoms. The target product of the photochlorination reaction in the present application means a product where hydrogen atoms on the alkyl groups in the aromatic compound are completely substituted by chlorine atoms.

The trichloromethyl-substituted benzene in the present application has a formula $(X)_a C_6 H_{6-a-b}(CCl_3)_b$, where X is a chlorine, bromine or fluorine atom, "a" is an integer selected from 0, 1, 2, 3, 4 and 5, "b" is an integer selected from 1, 2, 3 and 4, and a+b≤6.

In the reaction system according to the method of the present application, preferably, no solvent and initiator are added, and more preferably, no components other than the reactants are added. The purity of the products in the present application, particularly in the examples is quantitatively determined via gas chromatography (area normalization method) before the reaction mixture is subjected to separation. The yield in the photochlorination of the present application means a mass ratio of pure trichloromethyl-substituted benzene converted from crude trichloromethyl-substituted benzene to theoretically obtainable trichloromethyl-substituted benzene by chlorination reaction of the raw material aromatic compound. The yield in the purification (for example molecular distillation or rectification) of the present application means the yield after the purification.

At various stages in the method of the present application, the reaction progression may be monitored by conventional sampling and detection methods such as gas chromatography, so as to suitably adjust the parameters described above, thereby saving the reaction time. The description about the durations for three stages is not limiting and the reaction time at each stage may be freely adjusted depending on the monitored results of chlorination progression. The speed of feeding chlorine herein is not limited to a particular feeding rate. When the expression such as slowly, gradually is used to describe the speed of feeding chlorine, its meaning is not unclear, because the speed of feeding chlorine may be adjusted by those skilled in the art depending on the monitoring results of the reaction.

The product prepared by the method of the present application has a high purity value. In some embodiments, a mixture with a purity of about 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.5%, 89.0%, 89.5%, 90.0%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.1%, about 99.2%, about 99.3%, about 99.4%, about 99.5%, about 99.6%, about 99.7% or about 99.8% is directly obtained after the reaction. In some embodiments, a mixture with a purity of more than about 90.0%, about 90.5%, about 91.0%, about 91.5%, about 92.0%, about 92.5%, about 93.0%, about 93.5%, about 94.0%, about 94.5%, about 95.0%, about 95.5%, about 96.0%, about 96.5%, about 97.0%, about 97.5%, about 98.0%, about 98.5%, about 99.0%, about 99.1%, about 99.2%, about 99.3%, about 99.4%, about 99.5%, about 99.6%, about 99.7%, about 99.8% or about 99.9% is directly obtained after the reaction. In some embodiments, preferably, a mixture with a purity of 95.0%, 95.5%, 96.0%, 96.5%, 97.0%, 97.5%, 98.0%, 98.5%, 99.0%, 99.1%, 99.2%, 99.3%, 99.4%, 99.5%, 99.6%, 99.7%, 99.8% or 99.9% is directly obtained after the reaction. In some embodiments, preferably, a mixture with a purity of between about 90.0% and about 90.5%, between about 90.0% and about 91.0%, between about 90.0% and about 91.5%, between about 90.0% and about 92.0%, between about 90.0% and about 92.5%, between about 90.0% and about 93.0%, between about 90.0% and about 93.5%, between about 90.0% and about 94.0%, between about 90.0% and about 94.5%, between about 90.0% and about 95.0%, between about 90.0% and about 95.5%, between about 90.0% and about 96.0%, between about 90.0% and about 96.5%, between about 90.0% and about 97.0%, between about 90.0% and about 97.5%, between about 90.0% and about 98.0%, between about 90.0% and about 98.5%, between about 90.0% and about 99.0%, between about 90.0% and about 99.1%, between about 90.0% and about 99.2%, between about 90.0% and about 99.3%, between about 90.0% and about 99.4%, between about 90.0% and about 99.5%, between about 90.0% and about 99.6%, between about 90.0% and about 99.7%, between about 90.0% and about 99.8%, or between about 90.0% and about 99.9% is obtained after the reaction.

Trichloromethyl-substituted benzene in the present invention may be further purified via recrystallization, rectification or molecular distillation. Further, the present inventors also have found that trichloromethyl-substituted benzene obtained by chlorination is heat sensitive; and in particular, when such a substance is heated industrially for a long time using a metal-made apparatus, it easily suffers from dimerization and is converted into high-boiling-point impurity, thereby reducing the total yield of the target product. This problem can be well solved by the present invention using molecular distillation.

The molecular distillation method of the present invention comprises the following steps (1)-(3):

(1) pre-treating a crude trichloromethyl-substituted benzene (for example, bis-(trichloromethyl)-benzene) to remove light components therein;

(2) subjecting trichloromethyl-substituted benzene (for example, bis-(trichloromethyl)-benzene) pre-treated in step (1) to separation by distillation in a primary molecular distiller at a controlled molecular distillation temperature between 75° C. and 135° C. and absolute pressure between 3 Pa and 90 Pa, to obtain a primary distillate and a primary residue; and (3) collecting the primary distillate in step (2), to obtain purified trichloromethyl-substituted benzene (for example, bis-(trichloromethyl)-benzene), which may be optionally further purified.

The pre-treatment in step (1) of the molecular distillation method of the present invention is one of thin film evaporation, distillation or rectification. In an embodiment of the molecular distillation method of the present invention, in step (2), the residue in the primary molecular distiller is subjected to a secondary or multiple-stage molecular distillation as needed, to give distillates and residues therefrom; and accordingly; in step (3), the distillates of the stages in step (2) are collected and combined and optionally purified, to give purified trichloromethyl-substituted benzene (for example, bis-(trichloromethyl)-benzene).

In a preferred embodiment, the molecular distillation method of the present invention comprises the following steps (1)-(3):

(1) pre-treating a crude trichloromethyl-substituted benzene (for example, bis-(trichloromethyl)-benzene) to remove light components therein;

(2) operation a): subjecting trichloromethyl-substituted benzene (for example, bis-(trichloromethyl)-benzene) pre-treated in step (1) to separation by distillation in a primary molecular distiller at a controlled molecular distillation temperature between 75° C. and 135° C. and absolute pressure between 3 Pa and 90 Pa, to obtain a primary distillate and a primary residue;

operation b): subjecting the primary residue in operation a) into a secondary molecular distiller tower at a controlled molecular distillation temperature between 80° C. and 145° C. and absolute pressure between 3 Pa and 90 Pa to obtain a secondary distillate and a secondary residue;

(3) collecting and combining the primary distillate and the secondary distillate from operation a) and operation b) in step (2) to obtain purified trichloromethyl-substituted benzene (for example, bis-(trichloromethyl)-benzene), which may be optionally further purified.

In an embodiment of the molecular distillation method of the present invention, trichloromethyl-substituted benzene (for example, bis-(trichloromethyl)-benzene) is pre-treated using thin film evaporation at a temperature between 90° C. and 150° C. and a vacuum degree between 0.080 MPa and 0.098 MPa.

In a preferred embodiment, the purification method by molecular distillation of the present application uses bis-(trichloromethyl)-benzene as trichloromethyl-substituted benzene, and comprises the following steps (1)-(3):

(1) pre-treating a crude of bis-(trichloromethyl)-benzene to remove light components therein;

(2) subjecting bis-(trichloromethyl)-benzene pre-treated in step (1) to separation by distillation in a primary molecular distiller at a controlled molecular distillation temperature between 85° C. and 135° C. and absolute pressure between 10 Pa and 70 Pa, to obtain a primary distillate and a primary residue; and (3) collecting the primary distillate in the (2), to obtain purified bis-(trichloromethyl)-benzene, which may be optionally further purified.

In a preferred embodiment, the purification method by molecular distillation of the present application uses bis-(trichloromethyl)-benzene as trichloromethyl-substituted benzene, and comprises the following steps (1)-(3):

(1) pre-treating a crude bis-(trichloromethyl)-benzene to remove light components therein;

(2) operation a): subjecting bis-(trichloromethyl)-benzene pre-treated in the (1) to separation by distillation in a primary molecular distiller at a controlled molecular distillation temperature between 85° C. and 135° C. and absolute pressure between 10 Pa and 70 Pa, to obtain a primary distillate and a primary residue;

operation b): subjecting the primary residue in operation a) into a secondary molecular distiller tower at a controlled molecular distillation temperature between 95° C. and 145° C. and absolute pressure between 10 Pa and 70 Pa, to obtain a secondary distillate and a secondary residue;

(3) collecting and combining the primary distillate and the secondary distillate from operation a) and operation b) in step (2), to obtain purified bis-(trichloromethyl)-benzene, which may be optionally further purified.

The pre-treatment of the crude of bis-(trichloromethyl)-benzene in step (1) of the molecular distillation method of bis-(trichloromethyl)-benzene of the present invention is one of thin film evaporation, distillation or rectification.

In the molecular distillation method of bis-(trichloromethyl)-benzene of the present invention, bis-(trichloromethyl)-benzene is pre-treated using thin film evaporation at a controlled temperature between 90° C. and 150° C. and a vacuum degree between 0.080 MPa and 0.098 MPa.

In the molecular distillation method of the present application, the distillate in step (3) may further be purified as needed, for example by further molecular distillation, recrystallization and the like.

In the molecular distillation method of the present application, the light components removed in the pre-treatment step may optionally be separated and purified, and may be suitably used depending on the composition and purity thereof.

In the molecular distillation method of the present application, the molecular distillation process is achieved on a molecular distillation apparatus, and a complete set of the molecular distillation apparatus mainly comprises a feeding system, a molecular distiller, a distillate collection system, a heating system, a cooling system, a vacuum system, and a control system.

In the distillation method of the present application, a wiped-film molecular distiller is preferred. The main characteristic of the wiped-film molecular distiller is that it has a build-in condenser and is provided with a wiper, so that after a substance to be separated enters the molecular distillation apparatus, a uniform liquid film is formed under the action of the wiper, and then light components directly fly in a molecular state towards the build-in condenser on the center and condense into liquid to enter a light-components trap, while heavy fractions enter a heavy-fractions trap along an inner wall of an evaporator cylinder.

In the distillation method of the present application, the thin film evaporation is achieved on a vacuum thin film distillation apparatus.

The molecular distillation method of the present application is applicable to purification of all the chlorination reaction mixtures in the present application.

In some embodiments, after the reaction mixtures are purified by molecular distillation or single rectification, trichloromethyl-substituted benzene compounds with a purity of about 99.0%, about 99.1%, about 99.2%, about 99.3%, about 99.4%, about 99.5%, about 99.6%, about 99.7%, about 99.8%, about 99.9%, or about 99.95% can be obtained. The trichloromethyl-substituted benzene mixtures, for example bis-(trichloromethyl)-benzene mixtures, directly obtained by the method of the present invention comprise few low-boiling-point impurity, and thus can be purified by molecular distillation or rectification to obtain a high purity of trichloromethyl-substituted benzene products. They may also be purified by recrystallization to obtain trichloromethyl-substituted benzene compounds.

As described above, when "a" is 0 and "b" is 2, dimethylbenzene is a raw material, and a high purity of bis-(trichloromethyl)-benzene can be obtained according to the method of photochlorination of the present application. The resulting bis-(trichloromethyl)-benzene with a high purity can react with or without purification with phthalic acid in an industrialized reaction scale, so as to prepare a high purity of bis-(chloroformyl)-benzene. Preferably, purified bis-(trichloromethyl)-benzene with a high purity is used in the present application to react with phthalic acid or water so as to prepare a high purity of bis-(chloroformyl)-benzene.

Thus, still another aspect of the application relates to a method for preparing bis-(chloroformyl)-benzene, comprising the following steps:

a) preparing bis-(trichloromethyl)-benzene according to any of the methods of the present application, with or without purification such as rectification or recrystallization after the reaction is completed;

b) reacting bis-(trichloromethyl)-benzene in the step a) to prepare bis-(chloroformyl)-benzene. In step b), bis-(trichloromethyl)-benzene is preferably reacted with water or phthalic acid, more preferably with phthalic acid.

In a preferred aspect of the present application, step b) further comprises the following steps:

i) fully melting bis-(trichloromethyl)-benzene at elevated temperature, adding water or phthalic acid and a catalyst, and uniformly stirring;

ii) heating the reaction system, for example to the range of 90-125° C., to obtain the product bis-(chloroformyl)-benzene;

iii) optionally performing purification such as rectification or recrystallization.

Preferably, the step of purifying bis-(trichloromethyl)-benzene is present in step a). Bis-(trichloromethyl)-benzene and phthalic acid are dosed in step i) at a stoichiometric molar ratio, for example preferably 1:1.01-1.03. The catalyst in step i) is a Lewis acid, for example, aluminum trichloride, zinc chloride, ferric trichloride, preferably ferric trichloride, and when it is reacted with water in step i), preferably, a small amount of phthalic acid is present. The amount of the catalyst added in step i) is preferably from 0.2% to 0.3% of the mass of bis-(trichloromethyl)-benzene.

The method for preparing bis-(chloroformyl)-benzene by reacting bis-(trichloromethyl)-benzene with phthalic acid has the following beneficial effects: it has a simple process, short production cycle, no mediums such as solvent added, and less environmental pollution; and because bis-(trichloromethyl)-benzene has a very high purity itself, another raw material does not need to be phthalic acid with a high purity (99.99% or above, not general industrial-grade of 99.5%) similar to that used in the thionyl chloride process, which significantly reduces the production cost. In addition, the product can be purified by conventional methods such as single rectification or recrystallization; because the reaction conditions are strictly controlled in the photochlorination reaction, light components and impurity with a boiling point close to that of bis-(trichloromethyl)-benzene are greatly reduced, so that the product bis-(chloroformyl)-benzene prepared from the bis-(trichloromethyl)-benzene has a very high purity, for example up to about 99.95%, about 99.96%, about 99.97%, about 99.98% or about 99.99%, that is, the resulting bis-(chloroformyl)-benzene reaches polymer-grade.

Thus, in another aspect, the present application relates to a method for preparing bis-(chloroformyl)-benzene, comprising reacting bis-(trichloromethyl)-benzene with a purity of above 99% and preferably above 99.2% (for example, bis-(trichloromethyl)-benzene prepared by the present application) with industrial-grade phthalic acid with a purity of 99.5%. The technical effect of the method is that polymer-grade bis-(chloroformyl)-benzene of up to 99.95% can be obtained from the resulting product by simple purification such as single rectification.

In addition, the present invention also relates to a photochlorination reactor comprising a reactor cylinder (simply referred as cylinder) and a transparent tube (simply referred as tube) for placing a light source therein, fixed on the cylinder, characterized in that when the cylinder is transparent, a reflecting layer is disposed on an outer wall of the cylinder; when the cylinder is not transparent, a reflecting layer is disposed on an inner wall of the cylinder; when the tube has a closed end and an open end, the closed end is located in the reactor cylinder and the open end faces outward and radially extends through the reactor cylinder; and when the tube has two open ends, both ends radially extend through the reactor cylinder.

In the present application, the distance between adjacent tubes is 0.5-5 times, preferably 1-2 times of the cylinder diameter; the angle between adjacent tubes is between 0 degrees and 90 degrees, preferably 90 degrees; the tubes may be fixed on the reactor cylinder by welding or fasteners;

when the cylinder is transparent, the reflecting layer is a reflective membrane, tin foil or aluminum foil lining the outer wall of the cylinder, or plated metal having reflective effect, for example silver, zinc, iron; and when the cylinder is not transparent, the reflecting layer is glass or quartz lining the inner wall of the cylinder.

A corrosion-resistant granular filler is placed in the reactor cylinder of the present application; the filling height of the corrosion-resistant granular filler in the reactor cylinder is 1/3 to 2/3 of the height of the reactor cylinder; and the material of the corrosion-resistant granular filler may be selected from glass, quartz or polytetrafluoroethylene or the like. The reactor cylinder includes a material inlet, a chlorine inlet, a product outlet, an off-gas outlet, and a thermometer socket. The number of such a thermometer socket may be set depending on the reactor size or temperature monitoring requirement.

Further, the chlorine inlet in the present application is equipped with a gas distributor; the gas distributor may be selected for example as a linear or annular distributor provided with vent holes; and the off-gas outlet is connected to a condenser. After the off-gas passes through the condenser, reaction materials and/or part of the reaction product carried by the off-gas condense and may be returned to the reactor.

In the present application, when the cylinder is transparent, it may be made of glass or quartz; when the cylinder is not transparent, it may be made of steel or other metals, or a molding material of glass lined steel; and the tubes may be made of glass or quartz.

In the present application, a heat exchange jacket is disposed on the outer wall of the reactor cylinder, and/or a heat exchange device is disposed in the reactor cylinder, for example a coil.

In the present application, parts and components used in the reactor, such as valves, sealing rings, are preferably made of polytetrafluoroethylene.

In the present application, the expression 'extend through the reactor' means passing through and being exposed out of the outer wall of the cylinder or only embedded in the outer wall of the cylinder.

In the present application, for closed ends of the tubes in the reactor, the closing may be integrally achieved in the manufacture, or may be later achieved by using other means, for example, using a flange cover.

In the present application, when the tubes in the reactor have one open end or two open ends, the open ends may be closed as needed.

In the present application, when the material of the non-transparent reactor cylinder is glass lined steel, glass may not be required to line the inner wall of the cylinder.

Compared with the prior art, the photochlorination reactor of the present application has the following beneficial effects:

The cylinder may be constructed from a transparent or non-transparent material. When the cylinder is transparent, the reflecting layer is disposed on the outer wall of the transparent cylinder and when the cylinder is not transparent, the reflecting layer is disposed on the inner wall of the non-transparent cylinder; so that in both cases, light emitted by the light sources in the tubes can be reflected in the reaction cylinder, so as to enhance the illumination intensity and range in the cylinder, which fully ensures intensity and uniform distribution of the illumination throughout the reactor, thereby reducing the occurrence of side reactions during the photochlorination reaction. Transparent or not, the inner wall of the reactor cylinder contacting with the reactants has corrosion-resistant performance, thereby prolonging the lifetime of the reactor. For example, for the transparent cylinder, the reflecting layer is on the outer wall and the inner wall is quartz or glass, and for the non-transparent cylinder, the reflecting layer is on the inner wall and the inner wall is glass or quartz. Thus, the inner wall contacting with the reactants has corrosion-resistant performance in both cases.

In addition, the reflecting layer is provided on the outer wall of the reactor cylinder to effectively reduce light loss and illumination loss, thereby reducing the energy consumption compared with the prior art.

When the tube for placing the light source therein has a closed end and an open end, the closed end is located in the reactor cylinder and does not extend through the cylinder; and the opening end faces outward and extends through the reactor cylinder, so that damage to the tubes due to uneven expansion and contraction can be avoided. The tube is durable in use, and routine maintenance cost is reduced, which is particularly suitable for the photochlorination reaction having a high reaction temperature. When the reaction temperature is low, the tubes generally will not be damaged due to expansion and contraction, and thus either end or both ends of the tube are made to be extending through the reactor cylinder.

Chlorine is introduced through the gas distributor, and the corrosion-resistant granular filler placed in the reactor cylinder prolongs the retention time of chlorine in the liquid, thereby achieving better reaction effect.

The off-gas outlet is further connected to the condenser, and reaction materials and/or part of the reaction product carried by the off-gas may be returned to the reactor after condensing, which reduces material losses and facilitates subsequent off-gas treatment.

The photochlorination reactor of the present application can be used in the photochemical method for preparing trichloromethyl-substituted benzene of the present application.

Hereafter, the present application will be described with specific embodiments. These specific embodiments are illustrative, not limiting.

EXAMPLES

Materials and Methods

The purity of the products 1,3-bis-(trichloromethyl)-benzene, 1,4-bis-(trichloromethyl)-benzene, bis-(chloroformyl)-benzene, 1-chloro-4-(trifluoromethyl)benzene, and trifluoromethylbenzene was determined by gas chromatography.

The purify of the product 1,3,5-tris(trifluoromethyl)benzene in the examples below was determined by liquid chromatography.

The illuminance in the examples was determined by an illuminometer.

A single LED lamp used in the examples has a wavelength amplitude between 20 and 50 nm, and two or more LED lamps with identical or different wavelength may be used to form an integrated light source.

Example 1

Into a 500 ml four-necked flask equipped with a temperature measuring device and a condensation reflux device, 212.32 g of 1,3-dimethylbenzene was added and heated to 60° C. LED lamps were turned on for irradiation, with a central peak wavelength of incident light of 460 nm and an illuminance of 49000 Lux. Then, chlorine was fed to initiate the reaction while the feeding rate of chlorine was controlled so that the system temperature was no higher than 120° C. The amount of chlorine consumed was 290 g and the first reaction stage took 4 h and 35 min. After the illuminance was adjusted to 61000 Lux and the system temperature was increased to 145° C., chlorine continued to be fed. The amount of chlorine consumed was 290 g and the second reaction stage took 3 h and 30 min. Further, the illuminance was adjusted to 87000 Lux, and the system temperature was increased to 180° C. while feeding chlorine. Chlorine continued to be fed while maintaining the temperature at 180° C. The amount of chlorine consumed was 300 g and the third reaction stage took 5 h and 55 min. The total amount of chlorine consumed in the reaction was 880 g. A sample was taken from the resulting reaction mixture after the reaction was completed. The sample was analyzed by gas chromatography, with a purity of 1,3-bis-(trichloromethyl)-benzene of 97.61% (see chromatogram 1) and a product yield of 95.45%.

Example 2

Into a 500 ml four-necked flask, equipped with a temperature measuring device and a condensation reflux device, 206.17 g of 1,3-dimethylbenzene was added and heated to 80° C. LED lamps were turned on for irradiation, with central peak wavelength of incident light of 360 nm and an illuminance of 49000 Lux. Then, chlorine was fed to initiate the reaction while the feeding rate of chlorine was controlled so that the system temperature was no higher than 120° C. The amount of chlorine consumed was 280 g and the first reaction stage took 4 h and 30 min. After the illuminance was adjusted to 60000 Lux and the system temperature was increased to 140° C., chlorine continued to be fed. The amount of chlorine consumed was 280 g and the second reaction stage took 3 h and 55 min. After the illuminance was maintained at 60000 Lux and the system temperature was increased to 160° C., 320 g of chlorine continued to be fed. The third reaction stage took 16 h and 35 min. The total amount of chlorine consumed in the reaction was 880 g. A sample was taken from the resulting reaction mixture after the reaction was completed. The sample was analyzed by gas chromatography, with a purity of 1,3-bis-(trichloromethyl)-benzene of 96.28% and a product yield of 94.01%.

Example 3

Into a 500 ml four-necked flask, equipped with a temperature measuring device, a condensation reflux device and a solvent recovery device, 201.50 g of 1,3-dimethylbenzene and 100 g of carbon tetrachloride as a solvent were added and heated to 60° C. LED lamps were turned on for irradiation, with a central peak wavelength of incident light of 465 nm and an illuminance of 43000 Lux. Then, chlorine was fed to initiate the reaction while the feeding rate of chlorine was controlled so that the system temperature was no higher than 120° C. The amount of chlorine consumed was 270 g and the first reaction stage took 4 h and 30 min. After the illuminance was adjusted to 66000 Lux and the system temperature was increased to 145° C., chlorine continued to be fed. The amount of chlorine consumed was 270 g and the second reaction stage took 3 h and 30 min. After the illuminance was adjusted to 91000 Lux and the system temperature was increased to 180° C., 300 g of chlorine continued to be fed. The third reaction stage took 4 h and 50 min. The total amount of chlorine consumed in the reaction was 840 g. The recovered carbon tetrachloride solvent was 74 g. A sample was taken from the resulting reaction mixture after the reaction was completed. The sample was analyzed by gas chromatography, with a purity of 1,3-bis-(trichloromethyl)-benzene of 95.89%.

Example 4

Into a 500 ml four-necked flask, equipped with a temperature measuring device and a condensation reflux device, 202.12 g of 1,3-dimethylbenzene was added and heated to 60° C. LED lamps were turned on for irradiation, with a central peak wavelength of incident light of 405 nm and an illuminance of 31000 Lux. Then, chlorine was fed to initiate the reaction while the feeding rate of chlorine was controlled so that the system temperature was no higher than 120° C. The amount of chlorine consumed was 135 g and the first reaction stage took 3 h and 20 min. After the illuminance was adjusted to 58000 Lux and the system temperature was increased to 160° C., chlorine continued to be fed. The amount of chlorine consumed was 405 g and the second reaction stage took 4 h and 30 min. After the illuminance was adjusted to 86000 Lux and the system temperature was increased to 170° C., 300 g of chlorine continued to be fed. The third reaction stage took 4 h and 45 min. The total amount of chlorine consumed in the reaction was 840 g. A sample was taken from the resulting reaction mixture after the reaction was completed. The sample was analyzed by gas chromatography, with a purity of 1,3-bis-(trichloromethyl)-benzene of 95.03%.

Example 5

Into a 500 ml four-necked flask, equipped with a temperature measuring device and a condensation reflux device, 200.37 g of 1,3-dimethylbenzene was added and heated to 60° C. LED lamps were turned on for irradiation, with a central peak wavelength of incident light of 465 nm and an illuminance of 49000 Lux. Then, chlorine was fed to initiate the reaction while the feeding rate of chlorine was controlled so that the system temperature was no higher than 120° C. The amount of chlorine consumed was 270 g and the reaction took 4 h and 30 min. Then, after the illuminance was increased to 70000 Lux and the system temperature was increased to 160° C., chlorine continued to be fed. The amount of chlorine consumed was 570 g and the reaction took 25 h and 35 min. The total amount of chlorine consumed in the reaction was 840 g. A sample was taken from the resulting reaction mixture after the reaction was completed. The sample was analyzed by gas chromatography, with a purity of 1,3-bis-(trichloromethyl)-benzene of 95.17%.

Example 6

Into a 500 ml four-necked flask, equipped with a temperature measuring device and a condensation reflux device, 202.40 g of 1,3-dimethylbenzene was added and heated to 60° C. LED lamps were turned on for irradiation, with a central peak wavelength of incident light of 586 nm and an illuminance of 20000 Lux. Then, chlorine was fed to initiate the reaction while the feeding rate of chlorine was controlled so that the system temperature was no higher than 120° C. The amount of chlorine consumed was 270 g and the first reaction stage took 4 h and 50 min. The illuminance was adjusted to 67000 Lux, and the system temperature was increased to 135° C. while feeding chlorine. After feeding chlorine for a time period, the amount of chlorine consumed was 270 g. Then, the system temperature was increased to 180° C. while feeding chlorine, and then the illuminance was adjusted to 86000 Lux. Then, chlorine continued to be fed while maintaining the temperature at 180° C. The amount of chlorine consumed was 330 g and the second and third reaction stages took 10 h and 35 min in total. The total amount of chlorine consumed in the reaction was 870 g. A sample was taken from the resulting reaction mixture after the reaction was completed. The sample was analyzed by gas chromatography, with a purity of 1,3-bis-(trichloromethyl)-benzene of 91.32%.

Example 7

Into a 500 ml four-necked flask, equipped with a temperature measuring device and a condensation reflux device, 203.10 g of 1,3-dimethylbenzene was added. LED lamps were turned on for irradiation, with a central peak wavelength of incident light of 505 nm and an illuminance of 43000 Lux. The system temperature was gradually increased from 55° C., and chlorine was gradually fed so that the system temperature was controlled no higher than 120° C. The amount of chlorine consumed was 270 g and the first reaction stage took 4 h and 50 min. The illuminance was adjusted to 66000 Lux, and the system temperature was increased to 142° C. After feeding chlorine for a time period, the amount of chlorine consumed was 270 g. Then, the system temperature was increased to 180° C. while feeding chlorine, and then the illuminance was adjusted to 96000 Lux. Then, chlorine continued to be fed while maintaining the temperature at 180° C. The amount of chlorine consumed was 310 g and the second and third reaction stages took 9 h and 40 min in total. The total amount of chlorine consumed in the reaction was 850 g. A sample was taken from the resulting reaction mixture after the reaction was completed. The sample was analyzed by gas chromatography, with a purity of 1,3-bis-(trichloromethyl)-benzene of 93.28%.

Example 8

The reaction mixtures of the examples 1-7 were purified by single rectification to obtain purified 1,3-bis-(trichloromethyl)-benzene. Purified 1,3-bis-(trichloromethyl)-benzenes were analyzed by gas chromatography to have a purity of 99.42%, 99.28%, 99.26%, 99.24%, 99.28%, 99.06% or 99.20%, respectively.

Example 9

Into a 500 ml four-necked flask, equipped with a temperature measuring device, a condensation reflux device and a stirring device, 402.45 g of 1,3-bis-(trichloromethyl)-benzene with a purity of 99.42% was added and heated to be completely melt. 216.94 g of m-phthalic acid with a purity of 99.50% was added in 1.01 times of the mole number of 1,3-bis-(trichloromethyl)-benzene, and then 1.21 g of ferric chloride catalyst was added in 0.30% of the weight of 1,3-bis-(trichloromethyl)-benzene. The temperature was raised to 110° C. for 60 min, at which the reaction was completed. The resulting product was subjected to rectification to obtain purified 1,3-bis-(chloroformyl)-benzene. The results from gas chromatography show that purified 1,3-bis-(chloroformyl)-benzene has a purity of 99.97% (chromatogram 2).

Example 10

Into a 500 ml four-necked flask, equipped with a temperature measuring device, a condensation reflux device and a stirring device, 400.16 g of 1,3-bis-(trichloromethyl)-benzene with a purity of 99.20% was added and heated to be completely melt. 219.98 g of m-phthalic acid with a purity of 99.50% was added in 1.03 times the mole number of 1,3-bis-(trichloromethyl)-benzene, and then 0.80 g of ferric chloride catalyst was added in 0.20% of the weight of 1,3-bis-(trichloromethyl)-benzene. The temperature was raised to 105° C. for 30 min, at which the reaction was completed. The resulting product was subjected to rectification to obtain purified 1,3-bis-(chloroformyl)-benzene. The results from gas chromatography show that purified 1,3-bis-(chloroformyl)-benzene has a purity of 99.95%.

Example 11

Into a 500 ml four-necked flask, equipped with a temperature measuring device, a condensation reflux device and a stirring device, 400.12 g of 1,3-bis-(trichloromethyl)-benzene with a purity of 99.28% was added and heated to be completely melt. 217.82 g of m-phthalic acid with a purity of 99.50% was added in 1.02 times of the mole number of 1,3-bis-(trichloromethyl)-benzene, and then 1.00 g of ferric chloride catalyst was added in 0.25% of the weight of 1,3-bis-(trichloromethyl)-benzene. The temperature was raised to 100° C. for 45 min, at which the reaction was completed. The resulting product was subjected to rectification to obtain purified 1,3-bis-(chloroformyl)-benzene. The results from gas chromatography show that purified 1,3-bis-(chloroformyl)-benzene has a purity of 99.96%.

Example 12

Into a 500 ml four-necked flask, equipped with a temperature measuring device and a condensation reflux device, 208.4 g of 1,4-dimethylbenzene was added and heated to 60° C. LED lamps were turned on for irradiation, with a central peak wavelength of incident light of 460 nm and an illuminance of 49000 Lux. Then, chlorine was fed to initiate the reaction while the feeding rate of chlorine was controlled so that the system temperature was no higher than 120° C. The amount of chlorine consumed was 280 g and the first reaction stage took 4 h. After the illuminance was adjusted to 56000 Lux and the system temperature was increased to 155° C., the amount of chlorine consumed was 280 g and the second reaction stage took 3 h and 20 min. The system temperature was increased to 180° C. while feeding chlorine, and the illuminance was adjusted to 97000 Lux. Chlorine continued to be fed while maintaining the temperature at 180° C. The amount of chlorine consumed was 300 g and the third reaction stage took 6 h and 10 min. The total amount of chlorine consumed in the reaction was 860 g. A sample was taken from the resulting reaction mixture after the reaction was completed. The sample was analyzed by gas chromatography, with a purity of 1,4-bis-(trichloromethyl)-benzene of 97.75% (see chromatogram 3) and a product yield of 95.20%.

Example 13

Into a 500 ml four-necked flask, equipped with a temperature measuring device and a condensation reflux device, 200.00 g of 1,4-dimethylbenzene was added and heated to 60° C. LED lamps were turned on for irradiation, with a central peak wavelength of incident light of 465 nm and an illuminance of 49000 Lux. Then, chlorine was fed to initiate the reaction while the feeding rate of chlorine was controlled so that the system temperature was no higher than 120° C. The amount of chlorine consumed was 270 g and the first reaction stage took 5 h. After the illuminance was adjusted to 66000 Lux and the system temperature was increased to 143° C., the amount of chlorine consumed was 270 g and the second reaction stage took 3 h and 50 min. The system temperature was increased to 180° C. while feeding chlorine, and then the illuminance was adjusted to 90000 Lux. Chlorine continued to be fed while maintaining the temperature at 180° C. The amount of chlorine consumed was 300 g and the third reaction stage took 5 h and 25 min. The total amount of chlorine consumed in the reaction was 840 g. A sample was taken from the resulting reaction mixture after the reaction was completed. The sample was analyzed by gas chromatography, with a purity of 1,4-bis-(trichloromethyl)-benzene of 97.04% and a product yield of 94.11%.

Example 14

Into a 500 ml four-necked flask, equipped with a temperature measuring device, a condensation reflux device and a solvent recovery device, 200.16 g of 1,4-dimethylbenzene and 100 g of carbon tetrachloride as a solvent were added and heated to 60° C. LED lamps were turned on for irradiation, with a central peak wavelength of incident light of 405 nm and an illuminance of 43000 Lux. Then, chlorine was fed to initiate the reaction while the feeding rate of chlorine was controlled so that the system temperature was no higher than 120° C. The amount of chlorine consumed was 270 g and the first reaction stage took 4 h and 50 min. After the illuminance was adjusted to 66000 Lux and the system temperature was increased to 150° C., the amount of chlorine consumed was 270 g and the second reaction stage took 3 h and 55 min. After the illuminance was adjusted to 97000 Lux and the system temperature was increased to 180° C., 310 g of chlorine continued to be fed. The third reaction stage took 5 h. The total amount of chlorine consumed in the reaction was 850 g. The recovered carbon tetrachloride solvent was 63 g. A sample was taken from the resulting reaction mixture after the reaction was completed. The sample was analyzed by gas chromatography, with a purity of 1,4-bis-(trichloromethyl)-benzene of 96.02%.

Example 15

Into a 500 ml four-necked flask, equipped with a temperature measuring device and a condensation reflux device, 200.21 g of 1,4-dimethylbenzene was added and heated to 60° C. LED lamps were turned on for irradiation, with a central peak wavelength of incident light of 505 nm and an illuminance of 31000 Lux. Then, chlorine was fed to initiate the reaction while the feeding rate of chlorine was controlled so that the system temperature was no higher than 120° C. The amount of chlorine consumed was 135 g and the first reaction stage took 3 h and 55 min. After the illuminance was adjusted to 58000 Lux and the system temperature was increased to 150° C., the amount of chlorine consumed was 405 g and the second reaction stage took 4 h and 55 min. After the illuminance was adjusted to 86000 Lux and the system temperature was increased to 170° C., the amount of chlorine consumed was 310 g and the third reaction stage took 5 h and 20 min. The total amount of chlorine consumed in the reaction was 850 g. A sample was taken from the resulting reaction mixture after the reaction was completed. The sample was analyzed by gas chromatography, with a purity of 1,4-bis-(trichloromethyl)-benzene of 95.52%.

Example 16

Into a 500 ml four-necked flask, equipped with a temperature measuring device and a condensation reflux device, 203.21 g of 1,4-dimethylbenzene was added and heated to 60° C. LED lamps were turned on for irradiation, with a central peak wavelength of incident light of 360 nm and an illuminance of 49000 Lux. Then, chlorine was fed to initiate the reaction while the feeding rate of chlorine was controlled so that the system temperature was no higher than 120° C. The amount of chlorine consumed was 270 g and the reaction took 4 h and 25 min. Then, the illuminance was adjusted to 70000 Lux and the system temperature was raised to 140° C. The amount of chlorine consumed was 650 g and the reaction took 31 h in total. The total amount of chlorine consumed in the reaction was 920 g. A sample was taken from the resulting reaction mixture after the reaction was completed. The sample was analyzed by gas chromatography, with a purity of 1,4-bis-(trichloromethyl)-benzene of 96.64%.

Example 17

The reaction mixtures of the examples 12-16 were purified by single rectification to obtain purified 1,4-bis-(trichloromethyl)-benzene. Purified 1,4-bis-(trichloromethyl)-benzenes were analyzed by gas chromatography to have a purity of 99.45%, 99.38%, 99.36%, 99.22% or 99.32%, respectively.

Example 18

Into a 500 ml four-necked flask, equipped with a temperature measuring device, a condensation reflux device and a stirring device, 400.32 g of 1,4-bis-(trichloromethyl)-benzene with a purity of 99.45% was added and heated to be completely melt. 215.79 g of p-phthalic acid with a purity of 99.50% was added in 1.01 times of the mole number of 1,4-bis-(trichloromethyl)-benzene, and then 1.00 g of ferric chloride catalyst was added in 0.25% of the weight of 1,4-bis-(trichloromethyl)-benzene. The temperature was raised to 125° C. for 60 min, at which the reaction was completed. The resulting product was subjected to rectification to obtain purified 1,4-bis-(chloroformyl)-benzene. The results from gas chromatography show that purified 1,4-bis-(chloroformyl)-benzene has a purity of 99.96%. (See chromatogram 4)

Example 19

Into a 500 ml four-necked flask, equipped with a temperature measuring device, a condensation reflux device and a stirring device, 402.36 g of 1,4-bis-(trichloromethyl)-benzene with a purity of 99.22% was added and heated to be completely melt. 219.04 g of p-phthalic acid with a purity of 99.50% was added in 1.02 times of the mole number of 1,4-bis-(trichloromethyl)-benzene, and then 1.21 g of ferric chloride catalyst was added in 0.30% of the weight of 1,4-bis-(trichloromethyl)-benzene. The temperature was raised to 120° C. for 45 min, at which the reaction was completed. The resulting product was subjected to rectification to obtain purified 1,4-bis-(chloroformyl)-benzene.

The results from gas Chromatography show that purified 1,4-bis-(chloroformyl)-benzene has a purity of 99.95%.

Example 20

Into a 500 ml four-necked flask, equipped with a temperature measuring device, a condensation reflux device and a stirring device, 405.12 g of 1,4-bis-(trichloromethyl)-benzene with a purity of 99.32% was added and heated to be completely melt. 222.70 g of p-phthalic acid with a purity of 99.50% was added in 1.03 times of the mole number of 1,4-bis-(trichloromethyl)-benzene, and then 0.81 g of ferric chloride catalyst was added in 0.20% of the weight of 1,4-bis-(trichloromethyl)-benzene. The temperature was raised to 115° C. for 30 min, at which the reaction was completed. The resulting product was subjected to rectification to obtain purified 1,4-bis-(chloroformyl)-benzene. The results from gas chromatography show that purified 1,4-bis-(chloroformyl)-benzene has a purity of 99.96%.

Example 21

Into a 500 ml four-necked flask, equipped with a temperature measuring device and a condensation reflux device, 201.00 g of 1,3-dimethylbenzene was added. LED lamps were turned on for irradiation, with a central peak wavelength of incident light of 465 nm and an illuminance of 60000 Lux. The temperature was increased from 20° C., and chlorine was gradually fed so that the system temperature was controlled to be no higher than 120° C. The reaction took 20 h and the amount of chlorine consumed was 1200 g. A sample was taken from the resulting reaction mixture after the reaction was completed. The sample was analyzed by gas chromatography, and the result shows that the primary reaction product was a chlorination product of 1,3-dimethylbenzene as a mixture with 4-5 chlorine substitutions. (See chromatogram 5)

Example 22

Into a 500 ml four-necked flask, equipped with a temperature measuring device and a condensation reflux device, 200.30 g of 1,3-dimethylbenzene was added. LED lamps were turned on for irradiation, with a central peak wavelength of incident light of 460 nm and an illuminance of 43000 Lux. The temperature was increased from 20° C., and chlorine was gradually fed so that the system temperature was controlled to be no higher than 120° C. The amount of chlorine consumed was 270 g and the first reaction stage took 5 h and 55 min. The illuminance was adjusted to 63000 Lux and the system temperature was increased to 142° C. The amount of chlorine consumed was 270 g. The system temperature was increased to 180° C. while feeding chlorine, and then the illuminance was adjusted to 91000 Lux. Chlorine continued to be fed while maintaining the temperature at 180° C. The amount of chlorine consumed was 360 g. The second and third reaction stages took 12 h and 15 min in total. The total amount of chlorine consumed in the reaction was 900 g. A sample was taken from the resulting reaction mixture after the reaction was completed. The sample was analyzed by gas chromatography, with a purity of 1,3-bis-(trichloromethyl)-benzene of 88.93%. (See chromatogram 6)

Example 23

Into a 500 ml four-necked flask, equipped with a temperature measuring device and a condensation reflux device, 201.46 g of 1,3-dimethylbenzene was added. LED lamps were turned on for irradiation, with a central peak wavelength of incident light of 505 nm and an illuminance of 43000 Lux. The temperature was increased from 30° C., and chlorine was gradually fed so that the system temperature was controlled to be no higher than 120° C. The amount of chlorine consumed was 270 g and the first reaction stage took 5 h and 40 min. The illuminance was adjusted to 61000 Lux, and the system temperature was increased to 145° C. After feeding chlorine for a time period, the amount of chlorine consumed was 270 g. Then, the system temperature was increased to 180° C. while feeding chlorine, and then the illuminance was adjusted to 89000 Lux. Then, chlorine continued to be fed while maintaining the temperature at 180° C. The amount of chlorine consumed was 300 g and the second and third reaction stages took 11 h and 5 min in total. The total amount of chlorine consumed in the reaction was 840 g. A sample was taken from the resulting reaction mixture after the reaction was completed. The sample was analyzed by gas chromatography, with a purity of 1,3-bis-(trichloromethyl)-benzene of 89.44%.

Example 24

Into a 500 ml four-necked flask, equipped with a temperature measuring device and a condensation reflux device, 200.90 g of 1,3-dimethylbenzene was added. LED lamps were turned on for irradiation, with a central peak wavelength of incident light of 465 nm and an illuminance of 43000 Lux. The temperature was increased from 40° C., and chlorine was gradually fed so that the system temperature was controlled to be no higher than 120° C. The amount of chlorine consumed was 270 g and the first reaction stage took 5 h and 10 min. The illuminance was adjusted to 63000 Lux and the system temperature was increased to 142° C. After feeding chlorine for a time period, the amount of chlorine consumed was 270 g. The system temperature was increased to 180° C. while feeding chlorine, and then the illuminance was adjusted to 93000 Lux. Chlorine continued to be fed while maintaining at 180° C. The amount of chlorine consumed was 320 g. The second and third reaction stages took 10 h in total. The total amount of chlorine consumed in the reaction was 860 g. A sample was taken from the resulting reaction mixture after the reaction was completed. The sample was analyzed by gas chromatography, with a purity of 1,3-bis-(trichloromethyl)-benzene of 89.51%.

Example 25

Into a 500 ml four-necked flask, equipped with a temperature measuring device and a condensation reflux device, 199.08 g of 1,3-dimethylbenzene was added and heated to 60° C. LED lamps were turned on for irradiation, with a central peak wavelength of incident light of 405 nm and an illuminance of 10000 Lux. Then, chlorine was gradually fed to initiate the reaction while the system temperature was controlled to be no higher than 120° C. The amount of chlorine consumed was 270 g and the first reaction stage took 4 h and 55 min. The illuminance was adjusted to 56000 Lux, and the system temperature was increased to 133° C. After feeding chlorine for a time period, the amount of chlorine consumed was 270 g. Then, the system temperature was increased to 180° C. while feeding chlorine, and then the illuminance was adjusted to 97000 Lux. Then, chlorine continued to be fed while maintaining the temperature at 180° C. The amount of chlorine consumed was 300 g and the second and third reaction stages took 15 h and 20 min in total. The total amount of chlorine consumed in the reaction was 840 g. A sample was taken from the resulting reaction mixture after the reaction was completed. The sample was analyzed by gas chromatography, with a purity of 1,3-bis-(trichloromethyl)-benzene of 88.03%.

Example 26

Into a 500 ml four-necked flask, equipped with a temperature measuring device and a condensation reflux device, 200.60 g of 1,3-dimethylbenzene was added and heated to 60° C. LED lamps were turned on for irradiation, with a central peak wavelength of incident light of 586 nm and an illuminance of 5000 Lux. Then, chlorine was fed to initiate the reaction while the system temperature was controlled to be no higher than 120° C. The amount of chlorine consumed was 270 g and the first reaction stage took 5 h and 5 min. The illuminance was adjusted to 69000 Lux, and the system temperature was increased to 147° C. After feeding chlorine for a time period, the amount of chlorine consumed was 270 g. Then, the system temperature was increased to 180° C. while feeding chlorine, and then the illuminance was adjusted to 98000 Lux. Then, chlorine continued to be fed while maintaining at 180° C. The amount of chlorine consumed was 300 g and the second and third reaction stages took 18 h and 30 min in total. The total amount of chlorine consumed in the reaction was 840 g. A sample was taken from the resulting reaction mixture after the reaction was completed. The sample was analyzed by gas chromatography, with a purity of 1,3-bis-(trichloromethyl)-benzene of 78.70%.

Example 27

Into a 500 ml four-necked flask, equipped with a temperature measuring device and a condensation reflux device, 200.05 g of 1,3-dimethylbenzene was added and heated to 60° C. LED lamps were turned on for irradiation, with a central peak wavelength of incident light of 465 nm and an illuminance of 500 Lux. Then, chlorine was fed to initiate the reaction while the system temperature was controlled to be no higher than 120° C. The amount of chlorine consumed was 270 g and the first reaction stage took 5 h and 30 min. Then, the illuminance was adjusted to 69000 Lux and the system temperature was raised to 150° C. After feeding chlorine for a time period, the amount of chlorine consumed was 270 g. Then, the system temperature was increased to 180° C. while feeding chlorine, and then the illuminance was adjusted to 98000 Lux. Then, chlorine continued to be fed while maintaining the temperature at 180° C. The amount of chlorine consumed was 300 g, and the second and third reaction stages took 20 h and 25 min in total. The total amount of chlorine consumed in the reaction was 940 g. A sample was taken from the resulting reaction mixture after the reaction was completed. The sample was analyzed by gas chromatography, with a purity of 1,3-bis-(trichloromethyl)-benzene of 70.12%. (see chromatogram 7)

Example 28

Into a 500 ml four-necked flask, equipped with a temperature measuring device and a condensation reflux device, 200.00 g of 1,3-dimethylbenzene was added and heated to 110° C. LED lamps were turned on for irradiation, with a central peak wavelength of incident light of 405 nm and an illuminance of 60000 Lux. Then, chlorine was fed to initiate the reaction. After a time period, the temperature of the reaction were elevated dramatically and could not be controlled below 120° C., resulting in rapid carbonization/blackening and thus failure of the reaction.

Example 29

Into a 500 ml four-necked flask, equipped with a temperature measuring device and a condensation reflux device, 202.10 g of 1,3-dimethylbenzene was added and heated to 120° C. LED lamps were turned on for irradiation, with a central peak wavelength of incident light of 360 nm and an illuminance of 43000 Lux. Then, chlorine was fed to initiate the reaction. After a time period, the temperature of the reaction were elevated dramatically and could not be controlled below 120° C., resulting in rapid carbonization/blackening and thus failure of the reaction.

Example 30

Into a 500 ml four-necked flask, equipped with a temperature measuring device and a condensation reflux device, 171 g of p-chlorotoluene was added and heated to 65° C. LED lamps were turned on for irradiation, with a central peak wavelength of incident light of 412 nm and an illuminance of 30000 Lux. Then, chlorine was fed to initiate the reaction while the feeding rate of chlorine was controlled so that the system temperature was no higher than 120° C. The amount of chlorine consumed was 156 g and the first reaction stage took 3 h and 45 min. After the illuminance was adjusted to 54000 Lux and the system temperature was increased to 150° C., chlorine continued to be fed. The amount of chlorine consumed was 171 g and the second reaction stage took 3 h and 10 min. The total amount of chlorine consumed in the reaction was 327 g. A sample was taken from the resulting reaction mixture after the reaction was completed. The sample was analyzed by gas chromatography, with a purity of p-chloro-(trichloromethyl)-benzene of 95.17%.

Example 31

Into a 500 ml four-necked flask, equipped with a temperature measuring device and a condensation reflux device, 250 g of methylbenzene was added and heated to 60° C. LED lamps were turned on for irradiation, with a central peak wavelength of incident light of 465 nm and an illuminance of 41000 Lux. Then, chlorine was fed to initiate the reaction while the feeding rate of chlorine was controlled so that the system temperature was no higher than 120° C. The amount of chlorine consumed was 305 g and the first reaction stage took 3 h and 15 min. After the illuminance was adjusted to 58000 Lux and the system temperature was increased to 135° C., chlorine continued to be fed while maintaining the temperature at 135° C. The amount of chlorine consumed was 296 g and the second reaction stage took 2 h and 5 min. The total amount of chlorine consumed in the reaction was 601 g. A sample was taken from the resulting reaction mixture after the reaction was completed. The sample was analyzed by gas chromatography, with a purity of (trichloromethyl)-benzene of 96.83%.

Example 32

Into a 500 ml four-necked flask, equipped with a temperature measuring device and a condensation reflux device, 185.2 g of sym-trimethylbenzene was added and heated to 80° C. LED lamps were turned on for irradiation, with a central peak wavelength of incident light of 405 nm and an illuminance of 11000 Lux. Then, chlorine was fed to initiate the reaction while the feeding rate of chlorine was controlled so that the system temperature was no higher than 120° C. The amount of chlorine consumed was 325 g and the first reaction stage took 5 h and 10 min. After the illuminance was adjusted to 50000 Lux and the system temperature was increased to 160° C., chlorine continued to be fed while maintaining the temperature at 180° C. The amount of chlorine consumed was 311 g and the second reaction stage took 13 h and 10 min. Then, the illuminance was adjusted to 55000 Lux, and the system temperature was increased to 300° C. while feeding chlorine. Chlorine continued to be fed until complete chlorination was achieved. The amount of chlorine consumed was 449 g and the third reaction stage took 15 h and 10 min. The total amount of chlorine consumed in the reaction was 1085 g. A sample was taken from the resulting reaction mixture after the reaction was completed. The sample was analyzed by liquid chromatography, with a purity of sym-tris(trichloromethyl)-benzene of 91.7%.

Example 33

Three glass-lined reaction columns with a temperature measuring device, a reflux condenser, an illumination device of LED lamps, and a heating/cooling device were arranged in series to form a continuous photochlorination reaction apparatus, where the glass-lined reaction columns were sequentially the first column, the second column and the third column. After the reaction apparatus was subjected to preparatory stages such as pressure testing, leakage testing, cleaning, and drying, the initial startup was performed, and the feeding quantity was gradually increased. After the photochlorination reaction was stable, 1,3-dimethylbenzene was continuously added at a rate of 95 kg/h into the first column. The first column was controlled at a temperature between 80° C. to 120° C. by the heating/cooling device, with a central peak wavelength of incident light of 460 nm and an average illuminance between 20000 and 39000 Lux, while chlorine was fed at a flow rate of 135 kg/h from the bottom for continuous photochlorination reaction, where the heating or cooling rate was controlled so that the temperature of the first column was no higher than 120° C. The reaction solution in the first column overflowed from the bottom into the second column, with a central peak wavelength of incident light of 505 nm and an average illuminance between 40000 and 61000 Lux. The second column was controlled at a temperature between 135 and 145° C., and chlorine was fed at a flow rate of 128 kg/h into the second column. The reaction solution in the second column overflowed from the bottom into the third column, with a central peak wavelength of incident light of 586 nm and an average illuminance between 60000 and 86000 Lux. The third column was controlled at a temperature between 170 and 180° C., and chlorine was fed at a flow rate of 148 kg/h into the third column. The total amount of chlorine fed in the reaction system consisting of the three columns was 411 kg/h. A sample was taken from the resulting reaction mixture at the outlet of the third column. The sample was analyzed by gas chromatography, with a purity of 1,3-bis-(trichloromethyl)-benzene of 93.1%.

A part of the crude 1,3-bis-(trichloromethyl)-benzene was purified by rectification. The resulting crude 1,3-bis-(trichloromethyl)-benzene was pre-heated to 100° C. and continuously added at a rate of 300 kg/h to the middle of the first column from the group of three continuous rectification columns. The bottom (kettle) of the first column was heated with a heat transfer oil, so as to maintain the column-bottom temperature between 165 and 175° C., the column-middle temperature between 100 and 130° C. and the column-top temperature between 85 and 110° C. The first column had a vacuum degree of 0.09 MPa. Low-boiling-point components and a small amount of the primary component 1,3-bis-(trichloromethyl)-benzene flowed from the condenser of the first column, a part of which was returned to the top of the first column and a part of which was continuously sent to the middle of the second column. The bottom (kettle) of the second column was also heated with a heat transfer oil, so as to maintain the column-bottom temperature between 165 and 175° C., the column-middle temperature between 80 and 100° C. and the column-top temperature between 75 and 95° C. The second column had a vacuum degree of 0.09 MPa. Light components essentially free of the primary component 1,3-bis-(trichloromethyl)-benzene were obtained at the top of the second column. The bottom liquid in the first column and the bottom liquid in the second column were mixed and sent to the middle of the third column. The bottom of the third column was heated with a heat transfer oil, so as to maintain the column-bottom temperature between 270° C. and 290° C., the column-middle temperature between 180 and 190° C. and the column-top temperature between 150 and 160° C. The third column had a vacuum degree of 0.098 MPa. The condensate out of the condenser at the top of the third column was partially returned to the top of the third column and a part of the condensate flowed into the receiving tank as rectified 1,3-bis-(trichloromethyl)-benzene, with an 8-hour average flow rate of 236 kg/h. The residual liquid of the third column was discharged from the bottom for treatment. A sample was taken from the receiving tank of 1,3-bis-(trichloromethyl)-benzene. The sample was analyzed by gas chromatography, with a purity of 1,3-bis-(trichloromethyl)-benzene of 99.3% and an average yield of 84% for the 8-hour rectification for 1,3-bis-(trichloromethyl)-benzene.

An additional part of the crude 1,3-bis-(trichloromethyl)-benzene was purified by molecular distillation. The resulting crude 1,3-bis-(trichloromethyl)-benzene was pre-heated to 50° C. and continuously added at a rate of 300 kg/h to a glass-lined vacuum thin film evaporator. The evaporator was controlled at a temperature of 95° C. and a vacuum degree of 0.090 MPa. A part of the primary component 1,3-bis-(trichloromethyl)-benzene and a small amount of low-boiling-point components were vaporized and entered the condenser to be recovered as light components. Most of the primary component and high-boiling-point impurities were further continuously sent to a primary molecular distiller. The primary molecular distiller had an absolute pressure of 20 Pa and a distillation temperature of 95° C. A shell and tube condenser in the column had a cooling temperature of 40° C., at which the material flowing along the column wall escaped and was captured to obtain distilled 1,3-bis-(trichloromethyl)-benzene. In order to make the distillation more complete, the distillation residue still containing the primary component from the bottom of the primary molecular distiller was further sent to a secondary molecular distiller. The secondary molecular distiller had the same pressure as the primary molecular distiller, a distillation temperature of 105° C., and a cooling temperature of 40° C., and the distillation residue was discharged from the lower column at a flow rate of 20 kg/h for treatment. The distillate in primary molecular distiller and the distillate in secondary molecular distiller were combined, to obtain distilled 1,3-bis-(trichloromethyl)-benzene with a flow rate of 252 kg/h. A sample was taken and analyzed by gas chromatography, with a purity of 1,3-bis-(trichloromethyl)-benzene of 99.12% and an average yield of 89% for the 8-hour molecular distillation based on 1,3-bis-(trichloromethyl)-benzene.

Example 34

Three glass-lined reaction columns with a temperature measuring device, a reflux condenser, an illumination device of LED lamps, and a heating/cooling device were arranged in series to form a continuous photochlorination reaction apparatus, where the glass-lined reaction columns were sequentially the first column, the second column and the third column. After the reaction apparatus was subjected to preparatory stages such as pressure testing, leakage testing, cleaning, and drying, the initial startup was performed, and the feeding quantity was gradually increased. After the photochlorination reaction was stable, 1,4-dimethylbenzene was continuously added at a rate of 100 kg/h into the first column. The first column was controlled at a temperature between 80° C. and 120° C. by the heating/cooling device, with a central peak wavelength of incident light of 470 nm and an average illuminance between 25000 and 37000 Lux, while chlorine was fed at a flow rate of 140 kg/h from the bottom for continuous photochlorination reaction, where the heating or cooling rate was controlled so that the temperature of the first column was no higher than 120° C. The reaction solution in the first column overflowed from the bottom into the second column, with a central peak wavelength of incident light of 502 nm and an average illuminance between 45000 and 61000 Lux. The second column was controlled at a temperature of 135-145° C., and chlorine was fed at a flow rate of 150 kg/h into the second column. The reaction solution in the second column overflowed from the bottom into the third column, with a central peak wavelength of incident light of 555 nm and an average illuminance between 70000 and 85000 Lux. The third column was controlled at a temperature between 170 and 180° C., and chlorine was fed at a flow rate of 145 kg/h into the third column. The total amount of chlorine fed in the reaction system consisting of the three columns was 435 kg/h. A sample was taken from the resulting reaction mixture at the outlet of the third column. The sample was analyzed by gas chromatography, with a purity of 1,4-bis-(trichloromethyl)-benzene of 92.5%.

A part of the crude 1,4-bis-(trichloromethyl)-benzene was purified by rectification. The resulting crude 1,4-bis-(trichloromethyl)-benzene was pre-heated to 120° C. and continuously added at a rate of 300 kg/h to the middle of the first column from the group of three continuous rectification columns. The bottom (kettle) of the first column was heated with a heat transfer oil, so as to maintain the column-bottom temperature between 175 and 195° C., the column-middle temperature between 120 and 140° C. and the column-top temperature between 110 and 120° C. The first column had a vacuum degree of 0.09 MPa. Low-boiling-point components and a small amount of the primary component 1,4-bis-(trichloromethyl)-benzene flowed from the condenser of the first column, a part of which was returned to the top of the first column and a part of which was continuously sent to the middle of the second column. The bottom (kettle) of the second column was also heated with a heat transfer oil, so as to maintain the column-bottom temperature between 165 and 175° C., the column-middle temperature between 100 and 110° C. and the column-top temperature between 95 and 105° C. The second column had a vacuum degree of 0.09 MPa. Light components essentially free of the primary component 1,4-bis-(trichloromethyl)-benzene were obtained at the top of the second column. The bottom liquid in the first column and the bottom liquid in the second column were mixed and sent to the middle of the third column. The bottom of the third column was heated with a heat transfer oil, so as to maintain the column-bottom temperature between 280° C. and 300° C., the column-middle temperature between 180 and 190° C. and the column-top temperature between 150 and 160° C. The third column had a vacuum degree of 0.098 MPa. The condensate out of the condenser at the top of the third column was partially returned to the top of the third column and a part of the condensate flowed into the receiving tank as rectified 1,4-bis-(trichloromethyl)-benzene, with an 8-hour average flow rate of 230 kg/h. The residual liquid of the third column was discharged from the bottom for treatment. A sample was taken from the receiving tank of 1,4-bis-(trichloromethyl)-benzene. The sample was analyzed by gas chromatography, with a purity of 1,4-bis-(trichloromethyl)-benzene of 99.19% and an average yield of 82.2% for the 8-hour rectification for 1,4-bis-(trichloromethyl)-benzene.

An additional part of the crude 1,4-bis-(trichloromethyl)-benzene was purified by molecular distillation. The resulting crude 1,4-bis-(trichloromethyl)-benzene was pre-heated to 120° C. and continuously added at a rate of 300 kg/h to a glass-lined vacuum thin film evaporator. The evaporator was controlled at a temperature of 125° C. and a vacuum degree of 0.090 MPa. A part of the primary component 1,4-bis-(trichloromethyl)-benzene and a small amount of low-boiling-point components were vaporized and entered the condenser to be recovered as light components. Most of the primary component and high-boiling-point impurities were further continuously sent to a primary molecular distiller. The primary molecular distiller had an absolute pressure of 20 Pa and a distillation temperature of 115° C. A shell and tube condenser in the column had a cooling temperature of 100° C., at which the material flowing along the column wall escaped and was captured to obtain distilled 1,4-bis-(trichloromethyl)-benzene. In order to make the distillation more complete, the material liquid still containing the primary component from the bottom of the primary molecular distiller was further sent to a secondary molecular distiller. For capturing, the secondary molecular still had the same pressure as the primary molecular still, a distillation temperature of 127° C., and a cooling temperature of 100° C., and the distillation residue was discharged from the lower column for treatment. The distillate in primary molecular distiller and the distillate in secondary molecular distiller were combined, to obtain distilled 1,4-bis-(trichloromethyl)-benzene with an 8-hour average flow rate of 245 kg/h. A sample was taken and analyzed by gas chromatography, with a purity of 1,4-bis-(trichloromethyl)-benzene of 99.23% and an average yield of 87.6% for the 8-hour molecular distillation for 1,4-bis-(trichloromethyl)-benzene.

Example 35

Light source: an integrated light source consisting of several LED lamp beads with wavelengths between 360 nm and 586 nm, for example an integrated light source consisting of several LED lamp beads with wavelengths of 360 nm, 430 nm, 468 nm, 470 nm, 502 nm, 505 nm, 523 nm, 555 nm, 560 nm, 565 nm, 574 nm and 585 nm.

Into a 500 ml four-necked flask, equipped with a temperature measuring device and a condensation reflux device, 182 g of 1,3-dimethylbenzene was added and heated to 60°

C. The LED integrated light source was turned on for irradiation, with an illuminance of 10000 Lux. Then, chlorine was fed to initiate the reaction while the feeding rate of chlorine was controlled so that the system temperature was no higher than 120° C. The amount of chlorine consumed was 268 g and the first reaction stage took 4 h and 50 min. After the illuminance was adjusted to 50000 Lux and the system temperature was increased to 143° C., chlorine continued to be fed. The amount of chlorine consumed was 271 g and the second reaction stage took 11 h and 10 min. Further, the illuminance was adjusted to 50000 Lux, and the system temperature was increased to 179° C. while feeding chlorine. Chlorine continued to be fed while maintaining the temperature at 179° C. The amount of chlorine consumed was 211 g and the third reaction stage took 12 h and 30 min. The total amount of chlorine consumed in the reaction was 750 g. A sample was taken from the resulting reaction mixture after the reaction was completed. The sample was analyzed by gas chromatography, with a purity of 1,3-bis-(trichloromethyl)-benzene of 91.7%.

Example 36

Light source: an integrated light source consisting of several LED lamp beads with wavelengths between 430 nm and 586 nm, for example an integrated light source consisting of several LED lamp beads with wavelengths of 430 nm, 468 nm, 470 nm, 502 nm, 505 nm, 523 nm, 555 nm, 560 nm, 565 nm, 574 nm and 585 nm.

Into a 500 ml four-necked flask, equipped with a temperature measuring device and a condensation reflux device, 208 g of 1,3-dimethylbenzene was added and heated to 71° C. The LED integrated light source was turned on for irradiation, with an illuminance of 20000 Lux. Then, chlorine was fed to initiate the reaction while the feeding rate of chlorine was controlled so that the system temperature was no higher than 120° C. The amount of chlorine consumed was 280 g and the first reaction stage took 5 h and 10 min. After the illuminance was adjusted to 45000 Lux and the system temperature was increased to 140° C., chlorine continued to be fed. The amount of chlorine consumed was 290 g and the second reaction stage took 10 h and 5 min. Further, the illuminance was adjusted to 55000 Lux, and the system temperature was increased to 181° C. while feeding chlorine. Chlorine continued to be fed while maintaining the temperature at 181° C. The amount of chlorine consumed was 280 g and the third reaction stage took 12 h and 5 min. The total amount of chlorine consumed in the reaction was 850 g. A sample was taken from the resulting reaction mixture after the reaction was completed. The sample was analyzed by gas chromatography, with a purity of 1,3-bis-(trichloromethyl)-benzene of 93%.

Example 37

Into a 500 ml four-necked flask, equipped with a temperature measuring device and a condensation reflux device, 185 g of 1,3-dimethylbenzene was added. When the temperature of the reactant was 0° C., the LED lamps were turned on for irradiation, with a central peak wavelength of incident light of 465 nm and an illuminance of 20000 Lux. Then, chlorine was fed to initiate the reaction while the feeding rate of chlorine was controlled so that the system temperature was no higher than 120° C. The amount of chlorine consumed was 260 g and the first reaction stage took 10 h and 10 min. After the illuminance was adjusted to 35000 Lux and the system temperature was increased to 135° C., chlorine continued to be fed. The amount of chlorine consumed was 270 g and the second reaction stage took 12 h and 10 min. Further, the illuminance was adjusted to 55000 Lux, and the system temperature was increased to 180° C. while feeding chlorine. Chlorine continued to be fed while maintaining the temperature at 180° C. The amount of chlorine consumed was 228 g and the third reaction stage took 12 h and 20 min. The total amount of chlorine consumed in the reaction was 758 g. A sample was taken from the resulting reaction mixture after the reaction was completed. The sample was analyzed by gas chromatography, with a purity of 1,3-bis-(trichloromethyl)-benzene of 87.3%.

Example 38

Into a 500 ml four-necked flask, equipped with a temperature measuring device and a condensation reflux device, 210 g of 1,3-dimethylbenzene was added and heated to 10° C. LED lamps were turned on for irradiation, with a central peak wavelength of incident light of 460 nm and an illuminance of 18000 Lux. Then, chlorine was fed to initiate the reaction while the feeding rate of chlorine was controlled so that the system temperature was no higher than 120° C. The amount of chlorine consumed was 290 g and the first reaction stage took 9 h and 10 min. After the illuminance was adjusted to 33000 Lux and the system temperature was increased to 140° C., chlorine continued to be fed. The amount of chlorine consumed was 290 g and the second reaction stage took 11 h and 10 min. Further, the illuminance was adjusted to 50000 Lux, and the system temperature was increased to 180° C. while feeding chlorine. Chlorine continued to be fed while maintaining the temperature at 180° C. The amount of chlorine consumed was 285 g and the third reaction stage took 12 h and 30 min. The total amount of chlorine consumed in the reaction was 865 g. A sample was taken from the resulting reaction mixture after the reaction was completed. The sample was analyzed by gas chromatography, with a purity of 1,3-bis-(trichloromethyl)-benzene of 87.8%.

Example 39

Into a 500 ml four-necked flask, equipped with a temperature measuring device and a condensation reflux device, 201 g of 1,3-dimethylbenzene was added and heated to 60° C. LED lamps were turned on for irradiation, with a central peak wavelength of incident light of 465 nm and an illuminance of 2000 Lux. Then, chlorine was fed to initiate the reaction while the feeding rate of chlorine was controlled so that the system temperature was no higher than 120° C. The amount of chlorine consumed was 280 g and the first reaction stage took 6 h and 10 min. After the illuminance was adjusted to 10000 Lux and the system temperature was increased to 140° C., chlorine continued to be fed. The amount of chlorine consumed was 290 g and the second reaction stage took 12 h and 10 min. Further, the illuminance was adjusted to 50000 Lux, and the system temperature was increased to 180° C. while feeding chlorine. Chlorine continued to be fed while maintaining the temperature at 180° C. The amount of chlorine consumed was 250 g and the third reaction stage took 12 h and 10 min. The total amount of chlorine consumed in the reaction was 820 g. A sample was taken from the resulting reaction mixture after the reaction was completed. The sample was analyzed by gas chromatography, with a purity of 1,3-bis-(trichloromethyl)-benzene of 73.4%.

Example 40

Into a 500 ml four-necked flask, equipped with a temperature measuring device and a condensation reflux device, 203 g of 1,3-dimethylbenzene was added and heated to 60° C. LED lamps were turned on for irradiation, with a central peak wavelength of incident light of 460 nm and an illuminance of 4000 Lux. Then, chlorine was fed to initiate the reaction while the feeding rate of chlorine was controlled so that the system temperature was no higher than 120° C. The amount of chlorine consumed was 286 g and the first reaction stage took 5 h and 50 min. After the illuminance was adjusted to 15000 Lux and the system temperature was increased to 140° C., chlorine continued to be fed. The amount of chlorine consumed was 280 g and the second reaction stage took 12 h and 20 min. Further, the illuminance was adjusted to 55000 Lux, and the system temperature was increased to 180° C. while feeding chlorine. Chlorine continued to be fed while maintaining the temperature at 180° C. The amount of chlorine consumed was 264 g and the third reaction stage took 11 h and 30 min. The total amount of chlorine consumed in the reaction was 830 g. A sample was taken from the resulting reaction mixture after the reaction was completed. The sample was analyzed by gas chromatography, with a purity of 1,3-bis-(trichloromethyl)-benzene of 76.1%.

Example 41

The reaction mixtures of the examples 22-27 were purified by a single rectification to give purified 1,3-bis-(trichloromethyl)-benzene, with a purity of 99.02%, 99.1%, 99.18%, 99.12%, 99.01% and 89.7% respectively.

The reaction mixtures of the examples 30-32 were purified by a single rectification to give purified p-chloro(trichloromethyl)-benzene, (trichloromethyl)-benzene, and sym-tris(trichloromethyl)-benzene, with a purity of 99.8%, 99.9% and 99.43% respectively.

The reaction mixtures of the examples 35-40 were purified by a single rectification to give purified 1,3-bis-(trichloromethyl)-benzene, with a purity of 99.42%, 99.31%, 99.14%, 99.19%, 99.11% and 99.08% respectively.

Example 42

Figure 8:
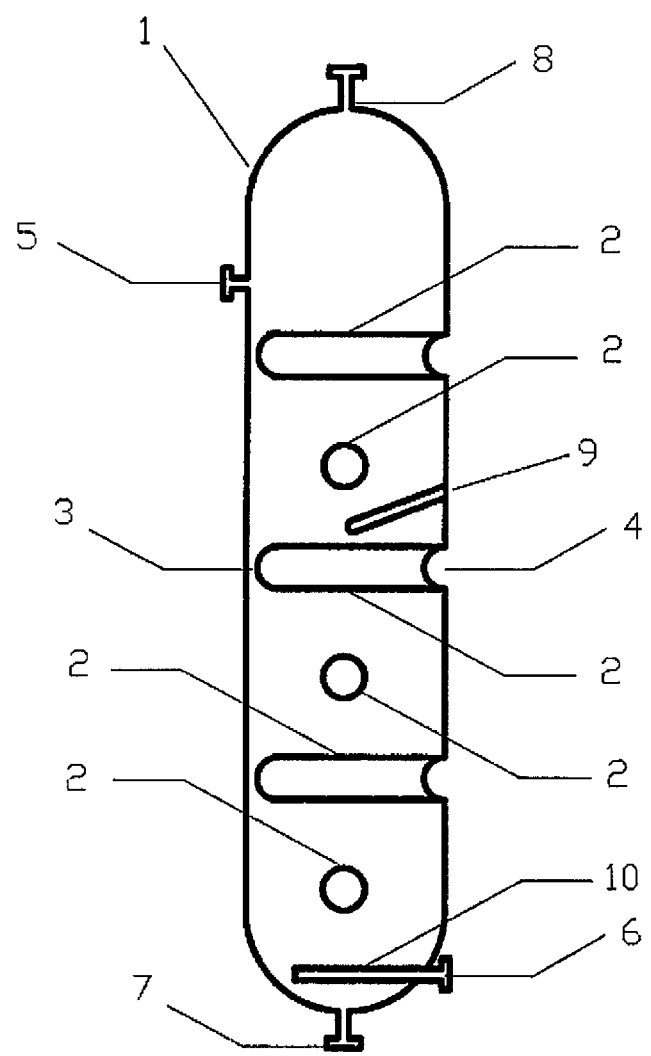
FIG. 8 is a schematic diagram of a photochlorination reactor of example 42.

The photochlorination reactor of the present invention (as shown in FIG. 8) comprises a reactor cylinder 1 and tubes 2 for placing a light source therein.

The reactor cylinder 1 is transparent, and a reflecting layer is disposed on an outer wall of the reactor cylinder 1. The reflecting layer is lined with a reflecting material, for example adhered with a reflective membrane, tin foil or aluminum foil or plated with a metal having reflective effect, for example silver, zinc, iron.

The tubes 2 for placing a light source are fixed on the reactor cylinder 1, and each has a closed end and an open end.

The closed end 3 is located in the reactor cylinder, and the open end faces outward and radially extends through the reactor cylinder 1. The tubes 2 may be fixed in the reactor cylinder 1 by welding or fasteners.

The angle between any adjacent tubes is between 0 degrees and 90 degrees and it is 90 degrees in this embodiment.

The distance between adjacent tubes is 0.5-5 times of the cylinder diameter, and it is 1 time in this embodiment.

A corrosion-resistant granular filler is placed in the reactor cylinder; the filling height of the granular filler in the reactor cylinder is preferably ⅓-⅔ of the height of the reactor cylinder; and the material of the corrosion-resistant granular filler may be selected from glass, quartz or polytetrafluoroethylene or the like. The corrosion-resistant granular filler in this embodiment is selected as glass beads and the filling height is half of the height of the cylinder.

The reactor cylinder 1 includes a material inlet 5, a chlorine inlet 6, a product outlet 7, an off-gas outlet 8, and a thermometer socket 9. The material inlet 5 and the thermometer socket 9 are located on a side wall of the reactor cylinder 1, the product outlet 7 is located at the bottom of the reactor cylinder 1, and the chlorine inlet 6 is located at the bottom the reactor cylinder above the product outlet 7.

The number of the thermometer socket may be set depending on the reactor size or temperature monitoring requirement, and is 1 in this embodiment.

The chlorine inlet 6 is equipped with a gas distributor 10; the gas distributor 10 may be selected for example as a linear or annular distributor provided with vent holes, as needed.

The materials for the reactor cylinder 1 and the tubes 2 for placing a light source therein are glass or quartz.

A heat exchange jacket is disposed on the outer wall of the reactor cylinder, and/or a coil is disposed in the reactor cylinder, for heat exchange.

Parts and components used in the reactor, such as valves, sealing rings, are preferably made of polytetrafluoroethylene.

The operating process of this example is as follows: the reaction material such as p-dimethylbenzene was fed to the reactor cylinder 1 from the material inlet 5; the light source such as LED lamp was placed in the tubes 2 and turned on; after the reaction was started, chlorine was fed to the reactor cylinder 1 from the chlorine inlet 6 through the gas distributor 10 and passed through the glass beads to react with p-dimethylbenzene; the reaction product was drawn from the product outlet 7; and the off-gas was discharged from the off-gas outlet 8 for collection and treatment.

Example 43

Figure 9:
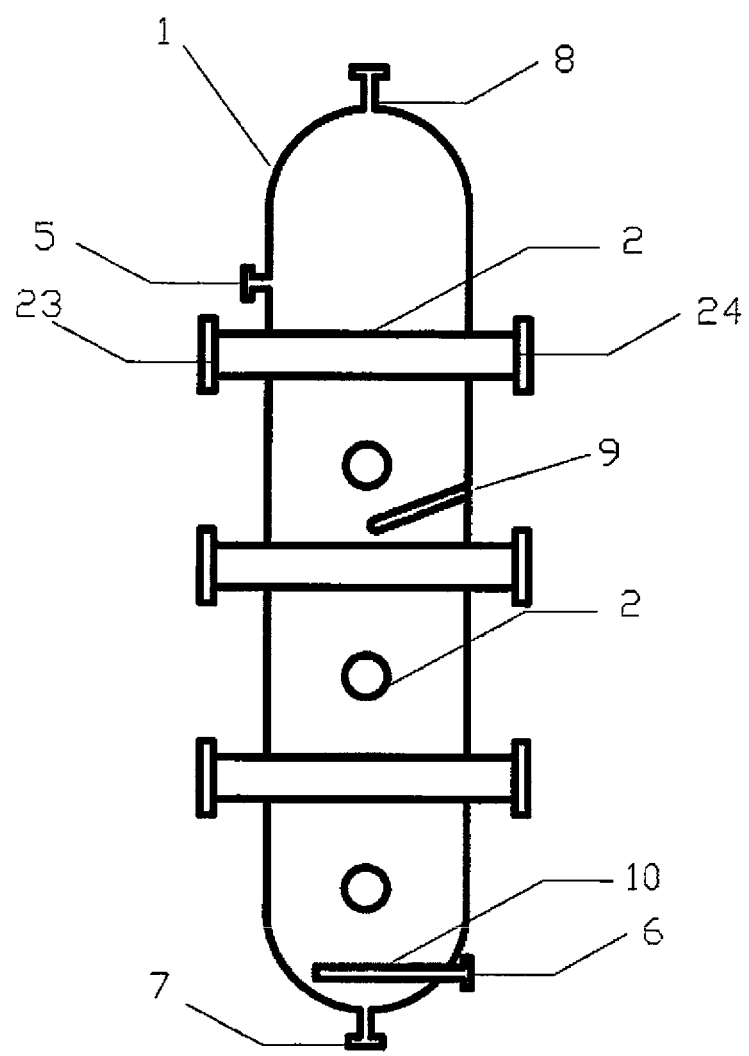
FIG. 9 is a schematic diagram of a photochlorination reactor of example 43.

The photochlorination reactor of the present invention has a structure as shown in FIG. 9 and this example differs from example 42 only in that both one end (23) and the other end (24) of each of the tubes is open and radially extends through the reactor cylinder.

When using the reactor of this example, the tubes also may each has one end closed and the other end open to facilitate the placement or removal of the light source; alternatively, both ends of the tubes may be closed after the light source is placed.

Example 44

This example differs from example 42 only in that the off-gas outlet 8 is connected to a condensing device, the angle between adjacent tubes is 45 degree, the corrosion-resistant granular filler is quartz granules, and the filling height is ⅔ of the height of the cylinder.

The operating process of this example is as follows: the reaction material such as m-dimethylbenzene was fed to the reactor cylinder 1 from the material inlet 5; the light source such as LED lamp was placed in the tubes and turned on; after the reaction was started, chlorine was fed to the reactor cylinder 1 from the chlorine inlet 6 through the gas distributor 10 and passed through the quartz granules to react with p-dimethylbenzene; the reaction product was drawn from the product outlet 7; the off-gas was discharged from the off-gas outlet 8 and passed through the condensing device for collection and treatment; and the condensate was returned to the reactor cylinder 1 for further reaction.

Example 45

This example differs from example 42 in that the reactor cylinder is not transparent. Steel or other metals are used as the cylinder material and a layer of glass or quartz is lined in an inner wall of the cylinder; and alternatively, glass-lined steel is directly used as the cylinder material without a reflecting layer lining the inner wall of the cylinder.

In this example, the tubes for placing the light source may be similar to those of embodiment 42 where one end extends through the cylinder or those of embodiment 43 where both ends extend through the cylinder, or a combination of the two.

In this example, the condensing device may or may not be disposed at the off-gas outlet as needed.

Specific embodiments of the photochlorination reactor of the present invention are described in embodiments 42-45. It should be understood that the photochlorination reactor of the present invention is not limited to these specific embodiments above, and various variations or modifications can be done by those skilled in the art within the scope of the claims, for example, with the change of the reactor size, relevant settings in the reactor: the numbers of the transparent tubes for placing a light source therein and the thermometer socket may be accordingly changed; with the development of material industry, new transparent materials suitable for the reactor cylinder and the tubes for placing the light source therein are developed; the positions of the tubes for placing the light source therein are changed; and so on. All of these changes belong to the scope of the present invention without affecting the essential content of the present invention.

What is claimed is:

1. A method for preparing trichloromethyl-substituted benzene, comprising
    feeding a chlorine at a starting reaction temperature between about 0° C. and about 85° C. and a starting illuminance between about 2000 Lux and about 55000 Lux,
    reacting an aromatic compound having a formula $(X)_aC_6H_{6-a-b}(CH_3)_b$ or a pendant alkyl chloride of the aromatic compound with the chlorine under illumination,
    controlling the reaction temperature to be no higher than about 120° C. at the illuminance at a first reaction stage, and
    continuing to feed the chlorine at a remaining reaction stage at a higher reaction temperature, under a higher illuminance, or both, than the first reaction stage, until the reaction is complete and trichloromethyl-substituted benzene is prepared,
    wherein X is a chlorine, bromine, or fluorine; a is 0, 1, 2, 3, 4, or 5; b is 1, 2, 3, or 4; a sum of a and b equals to or is less than 6,
    the illumination has a wavelength between about 350 nm and 700 nm and a wavelength amplitude of no more than 200 nm,
    the pendant alkyl group of the pendant alkyl chloride of the aromatic compound has at least one hydrogen atom that is not substituted by chlorine, and
    the process is conducted intermittently or continuously.

2. The method of claim 1, wherein the aromatic compound is m-dimethylbenzene or p-dimethylbenzene.

3. The method of claim 1, wherein the amount of chlorine consumed at the first reaction stage is at least about ⅙ of the total amount of required chlorine in the reaction.

4. The method of claim 1, wherein the first reaction stage is performed at the reaction temperature between about 55° C. and about 85° C. and the illuminance between 5000 Lux and about 55000 Lux.

5. The method of claim 1, wherein during the remaining reaction stage, the chlorine is fed at a higher reaction temperature and at a higher illuminance than the reaction temperature and illuminance at the first reaction stage;
    the reaction temperature during the remaining reaction stage is no higher than about 350° C.; and
    the illuminance during the remaining reaction stage is no more than about 100000 Lux.

6. The method of claim 5, wherein the remaining reaction stage is divided into a second reaction stage and a third reaction stage;
    the second reaction stage is performed at a reaction temperature no higher than about 160° C. and higher than the reaction temperature at the first reaction stage and at an illuminance no more than about 70000 Lux and higher than the illuminance at the first reaction stage; and
    the third reaction stage is performed at a reaction temperature no higher than about 350° C. and higher than the reaction temperature at the second reaction stage and at an illuminance no more than about 100000 Lux and higher than the illuminance at the second reaction stage.

7. The method of claim 6, wherein the second reaction stage is performed at the reaction temperature no lower than about 120° C. and the illuminance no less than about 10000 Lux.

8. The method of claim 6, wherein the third reaction stage is performed at the reaction temperature no lower than about 160° C. and the illuminance no less than about 50000 Lux.

9. The method of claim 6, wherein the amount of chlorine consumed in the second reaction stage is about ¼ to about ⅖ of the total amount of chlorine consumed in the reaction.

10. The method of claim 9, wherein the amount of chlorine consumed in each of the first, second, and third reaction stages is about ⅓ of the total amount of chlorine consumed in the reaction.

11. The method of claim 1, wherein a light source for the illumination is an LED lamp.

12. The method of claim 11, wherein the LED lamp is a blue LED lamp with a wavelength between 460 nm and 490 nm.

13. The method of claim 11, wherein the light source has a wavelength amplitude of no more than about 50 nm.

14. The method of claim 1, wherein no solvent and initiator are added in the reaction system during the reaction.

15. The method of claim 1, further comprising purifying the trichloromethyl-substituted benzene by molecular distillation, rectification, or recrystallization.

16. The method of claim 15, wherein the trichloromethyl-substituted benzene is purified by
    pretreating trichloromethyl-substituted benzene to remove light components;
    distilling the pretreated trichloromethyl-substituted benzene in a primary molecular distiller at a controlled temperature between 75° C. and 135° C. and absolute pressure between 3 Pa and 90 Pa, to obtain a primary distillate and a primary residue;

collecting the primary distillate to obtain purified trichloromethyl-substituted benzene; and
optionally further purifying the primary distillate.

17. The method of claim 16, further comprising
distilling the primary residue in a secondary molecular distiller at a controlled temperature between 80° C. and 145° C. and absolute pressure between 3 Pa and 90 Pa, to obtain a secondary distillate and a secondary residue,
collecting and combining the primary distillate and the secondary distillate to obtain purified trichloromethyl-substituted benzene, and
optionally purifying the combined trichloromethyl-substituted benzene.

18. The method of claim 16, wherein the trichloromethyl-substituted benzene is bis-(trichloromethyl)-benzene, and
the temperature in the primary molecular distiller is controlled at between 85° C. and 135° C. and absolute pressure between 10 Pa and 70 Pa to obtain the primary distillate and the primary residue.

19. The method of claim 18, further comprising
distilling the primary residue in a secondary molecular distiller at a controlled temperature between 95° C. and 145° C. and absolute pressure between 10 Pa and 70 Pa, to obtain a secondary distillate and a secondary residue,
collecting and combining the primary distillate and the secondary distillate to obtain purified bis-(trichloromethyl)-benzene, and
optionally purifying the combined bis-(trichloromethyl)-benzene.

20. The method of claim 16, wherein the trichloromethyl-substituted benzene is pretreated by thin film evaporation, distillation, or rectification.

21. The method of claim 20, wherein the trichloromethyl-substituted benzene is pretreated by using thin film evaporation at a controlled thin film evaporation temperature between 90° C. and 150° C. and a vacuum degree between 0.080 MPa and 0.098 MPa.

22. A method for preparing bis-(chloroformyl)-benzene according to claim 16, comprising:
reacting the bis-(trichloromethyl)-benzene prepared by the method of claim 16 with water or phthalic acid to prepare bis-(chloroformyl)-benzene.

23. The method of claim 22, further comprising
fully melting the bis-(trichloromethyl)-benzene at an elevated temperature,
adding water or phthalic acid and a catalyst to the melt bis-(trichloromethyl)-benzene to form a mixture and uniformly stirring the mixture,
heating the mixture and obtaining the bis-(chloroformyl)-benzene, and
optionally purifying the bis-(chloroformyl)-benzene.

24. The method of claim 23, wherein the catalyst is a Lewis acid, and a small amount of phthalic acid is present in the reaction along with the water and the catalyst.

25. The method of claim 23, wherein the bis-(trichloromethyl)-benzene has a purity of above 99% and the phthalic acid has a purity of 99.5% and is industrial grade.

* * * * *